(12) United States Patent
Nishikubo et al.

(10) Patent No.: US 9,375,754 B2
(45) Date of Patent: *Jun. 28, 2016

(54) LAMINATED PIEZOELECTRIC BODY, LAMINATED PIEZOELECTRIC BODY MANUFACTURING METHOD, AND ULTRASOUND TRANSDUCER AND ULTRASOUND DIAGNOSTIC DEVICE USING LAMINATED PIEZOELECTRIC BODY

(75) Inventors: Yuichi Nishikubo, Tokyo (JP); Kenji Ohnuma, Tokyo (JP); Kiyokazu Morita, Tokyo (JP); Kenji Suzuki, Tokyo (JP); Hidekazu Kodama, Tokyo (JP); Munehiro Date, Tokyo (JP)

(73) Assignee: KONICA MINOLTA MEDICAL & GRAPHIC, INC., Tokyo (JP)

( * ) Notice: Subject to any disclaimer, the term of this patent is extended or adjusted under 35 U.S.C. 154(b) by 114 days.

This patent is subject to a terminal disclaimer.

(21) Appl. No.: 13/637,850

(22) PCT Filed: Feb. 23, 2011

(86) PCT No.: PCT/JP2011/001033
§ 371 (c)(1),
(2), (4) Date: Sep. 27, 2012

(87) PCT Pub. No.: WO2011/121882
PCT Pub. Date: Oct. 6, 2011

(65) Prior Publication Data
US 2013/0018266 A1    Jan. 17, 2013

(30) Foreign Application Priority Data

Mar. 31, 2010 (JP) .................................. 2010-084018
Mar. 31, 2010 (JP) .................................. 2010-084533

(51) Int. Cl.
*A61B 8/14* (2006.01)
*B06B 1/06* (2006.01)
(Continued)

(52) U.S. Cl.
CPC ............. *B06B 1/0611* (2013.01); *A61B 8/4483* (2013.01); *A61B 8/4488* (2013.01); *G01S 7/52079* (2013.01); *H01L 41/083* (2013.01); *Y10T 29/42* (2015.01)

(58) Field of Classification Search
None
See application file for complete search history.

(56) References Cited

U.S. PATENT DOCUMENTS 3,271,622 A * 9/1966 Malagodi .............. H01L 41/107
310/331
5,034,649 A * 7/1991 Chida et al. .................... 310/332
(Continued)

FOREIGN PATENT DOCUMENTS

JP        64-77298      3/1989
JP        4-211600      8/1992
(Continued)

OTHER PUBLICATIONS

Fundamentals of Piezoelectric Materials Science, line 13 of p. 62 to line 10 of p. 64 (Japanese).
(Continued)

*Primary Examiner* — Katherine Fernandez
*Assistant Examiner* — Farshad Negarestan
(74) *Attorney, Agent, or Firm* — Lucas & Mercanti, LLP

(57) ABSTRACT

In a laminated piezoelectric body, a laminated piezoelectric body manufacturing method, an ultrasound transducer, and an ultrasound diagnostic device according to the present invention, a plurality of mutually laminated piezoelectric bodies are electrically connected in parallel to each other, and each of the plurality of piezoelectric bodies arranges an orientation of residual polarization or a crystal axis that is related to an electrical displacement or a sign of an electric field due to a direct piezoelectric effect in a direction which reduces sensitivity in a first resonance mode and increases sensitivity in a second resonance mode of a higher order than the first resonance mode with respect to an axis of a first-level piezoelectric body on a fixed end-side.

14 Claims, 24 Drawing Sheets

(51) Int. Cl.
*A61B 8/00* (2006.01)
*G01S 7/52* (2006.01)
*H01L 41/083* (2006.01)
*H04R 31/00* (2006.01)

(56) References Cited

U.S. PATENT DOCUMENTS

| | | | |
|---|---|---|---|
| 5,925,971 A * | 7/1999 | Unami | H03H 9/1014 310/328 |
| 6,663,565 B2 * | 12/2003 | Kawagishi et al. | 600/437 |
| 2002/0156379 A1 * | 10/2002 | Angelsen et al. | 600/459 |
| 2008/0021328 A1 * | 1/2008 | Habu et al. | 600/459 |
| 2008/0103395 A1 * | 5/2008 | Habu et al. | 600/459 |

FOREIGN PATENT DOCUMENTS

| | | |
|---|---|---|
| JP | 5-243632 | 9/1993 |
| JP | 2002-11004 | 1/2002 |
| JP | 2003-133898 | 5/2003 |
| JP | 2003-225237 | 8/2003 |
| JP | 4192598 | 10/2008 |
| WO | 2008/015917 | 2/2008 |

OTHER PUBLICATIONS

Partial English translation of Fundamentals of Piezoelectric Materials Science.

* cited by examiner

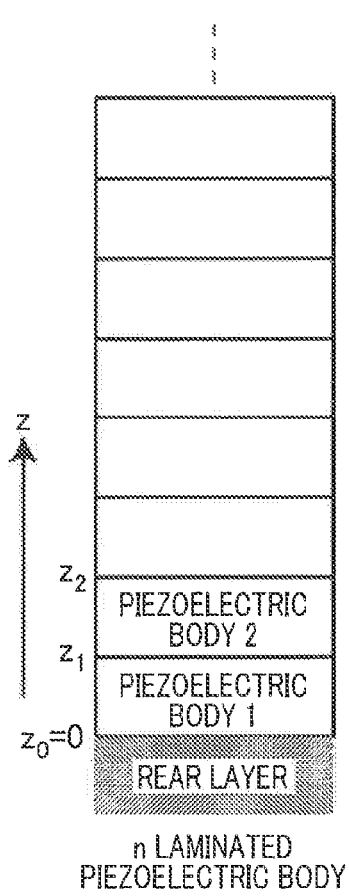
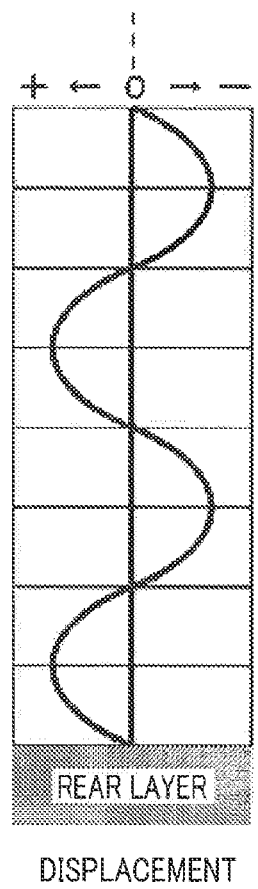
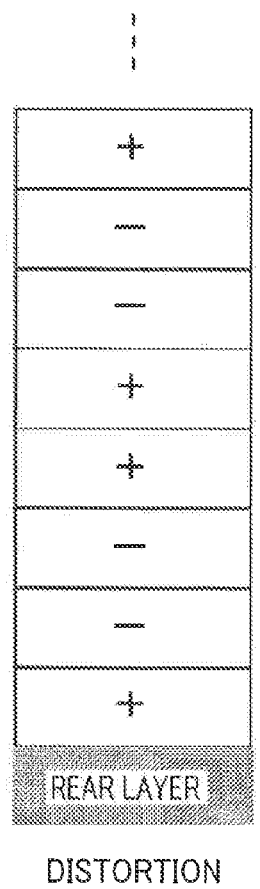
FIG.7A  n LAMINATED PIEZOELECTRIC BODY
FIG.7B  DISPLACEMENT
FIG.7C  DISTORTION

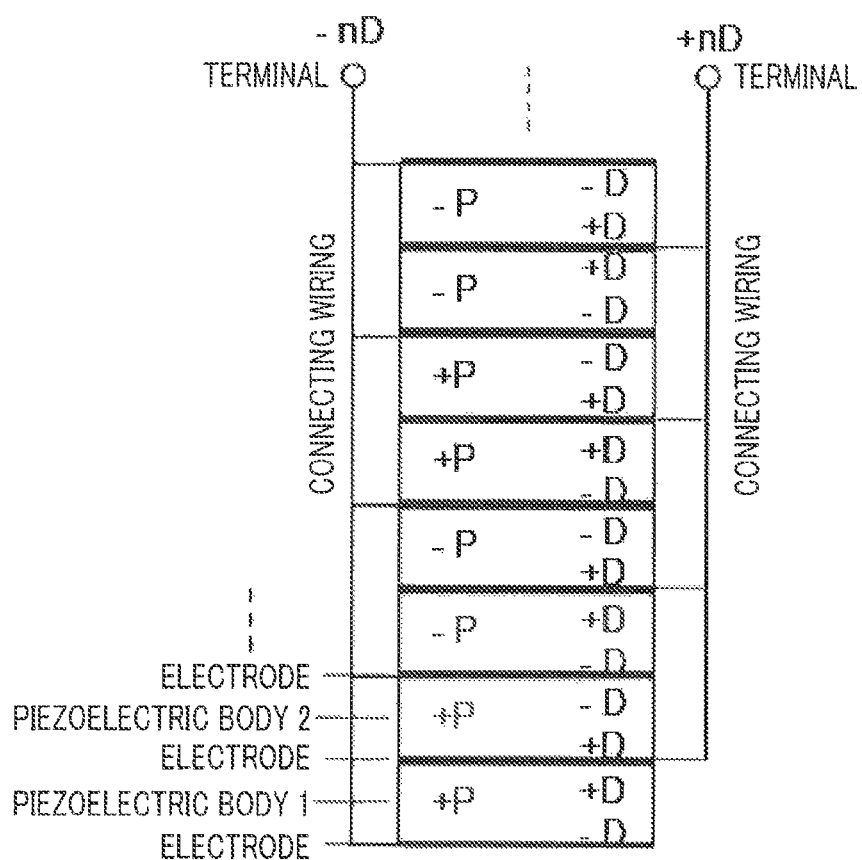

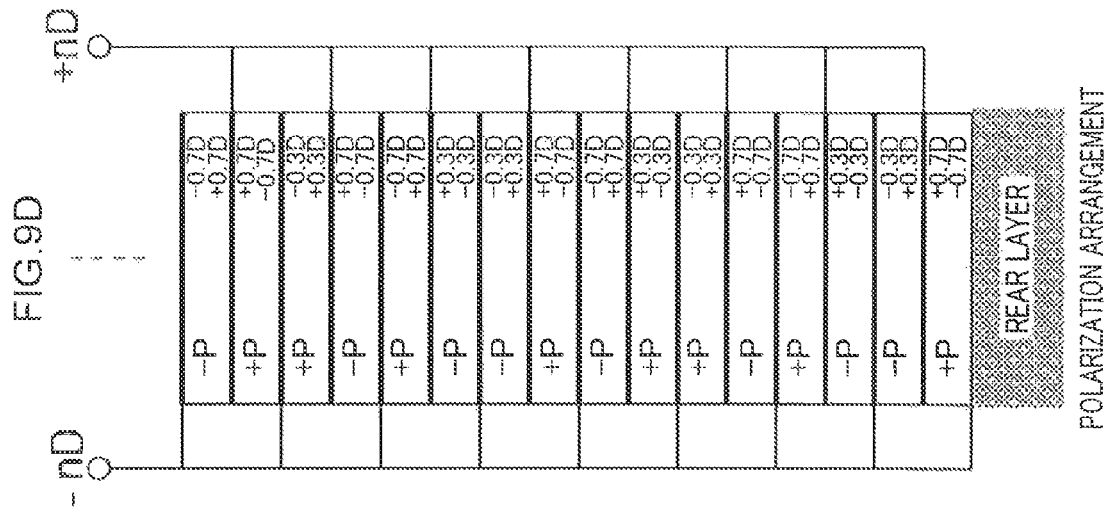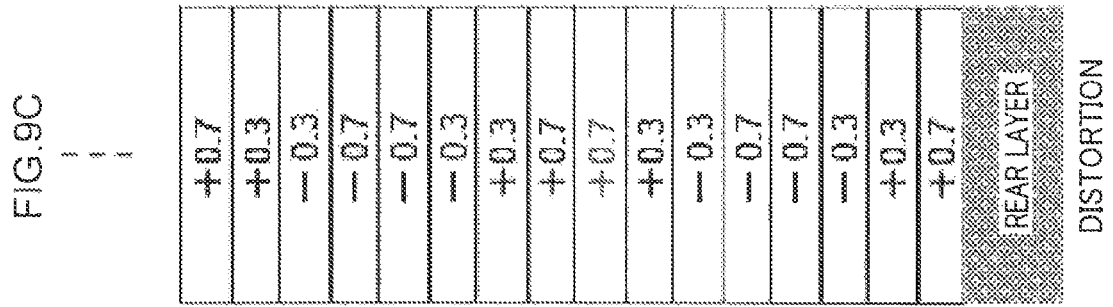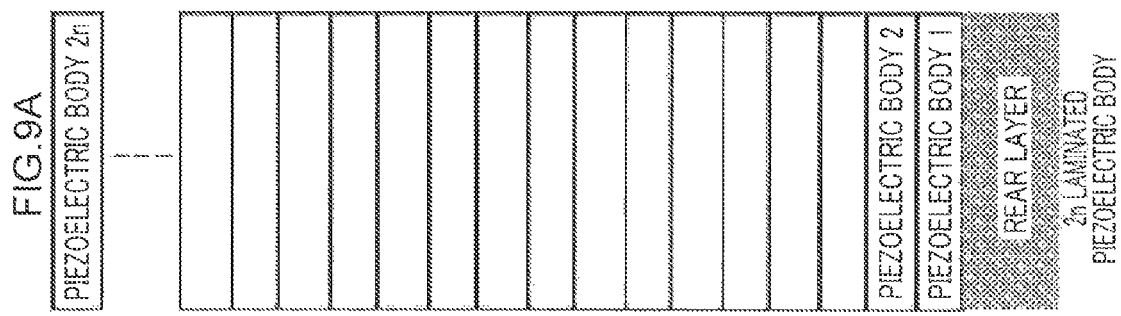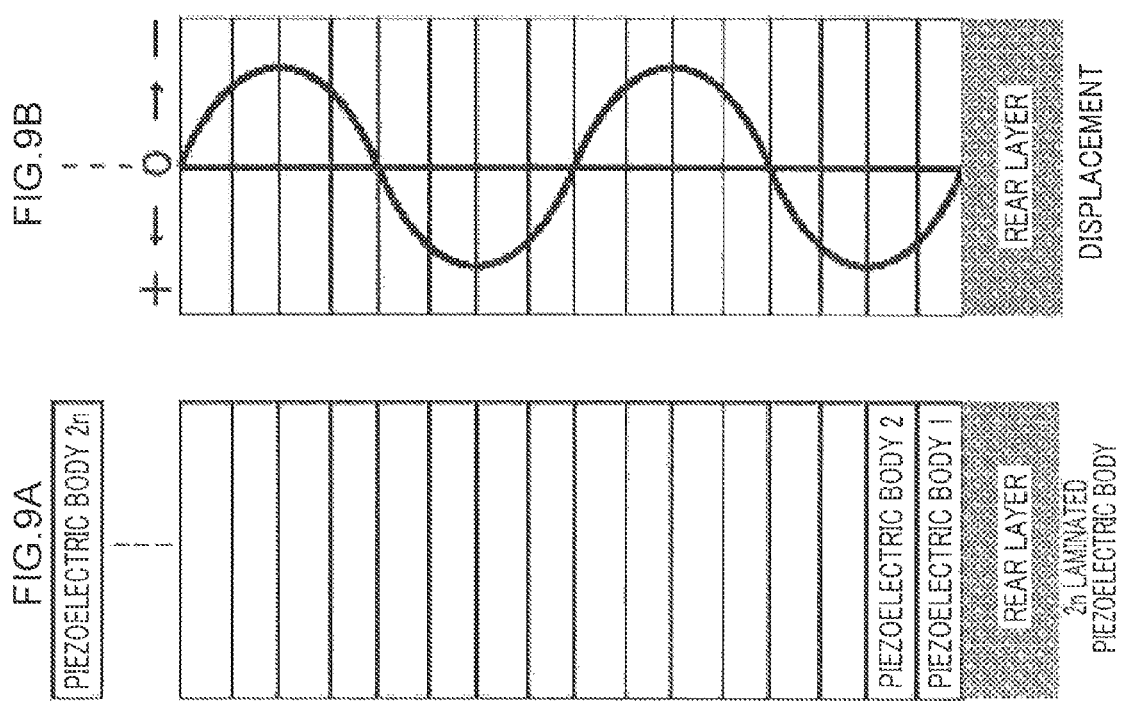

FIG.10
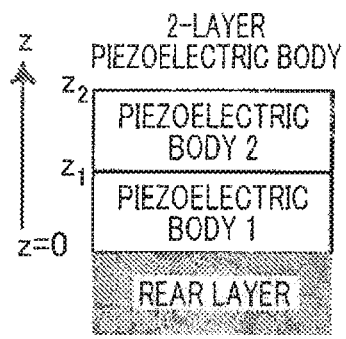
FIG.11A  FIG.11B
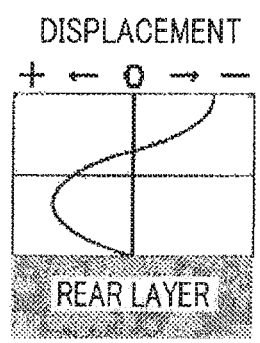 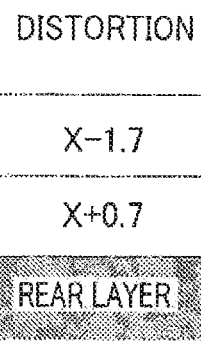

FIG.14
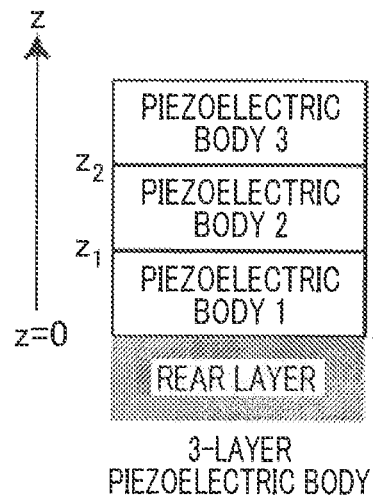
3-LAYER
PIEZOELECTRIC BODY
FIG.15A                FIG.15B
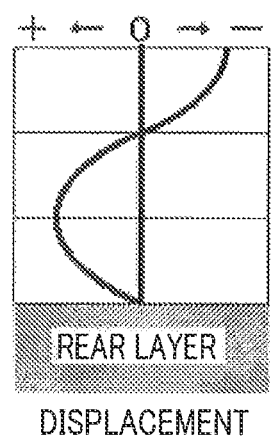    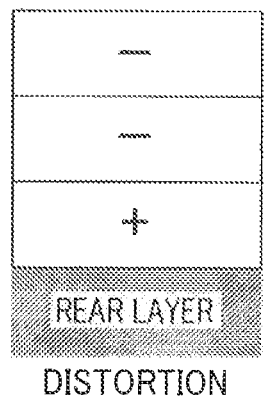
DISPLACEMENT           DISTORTION

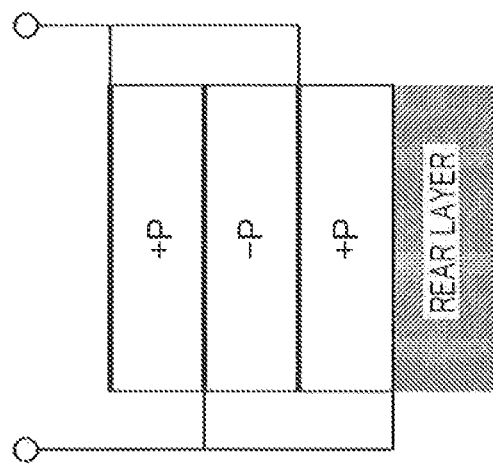
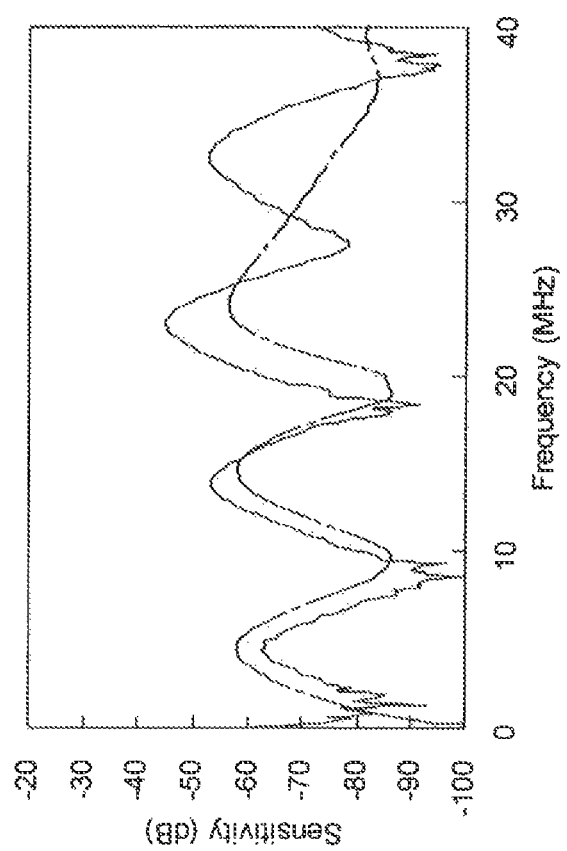
FIG. 18

6-LAYER
PIEZOELECTRIC BODY

DISPLACEMENT

DISTORTION

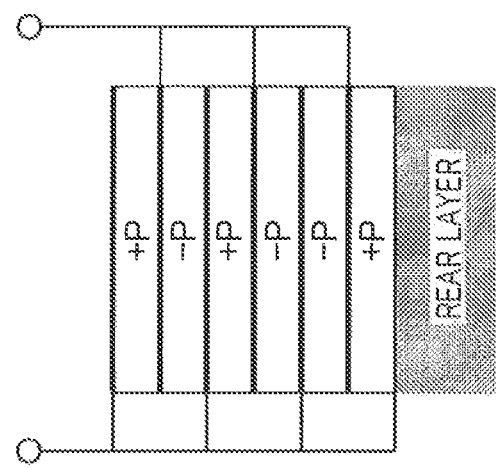
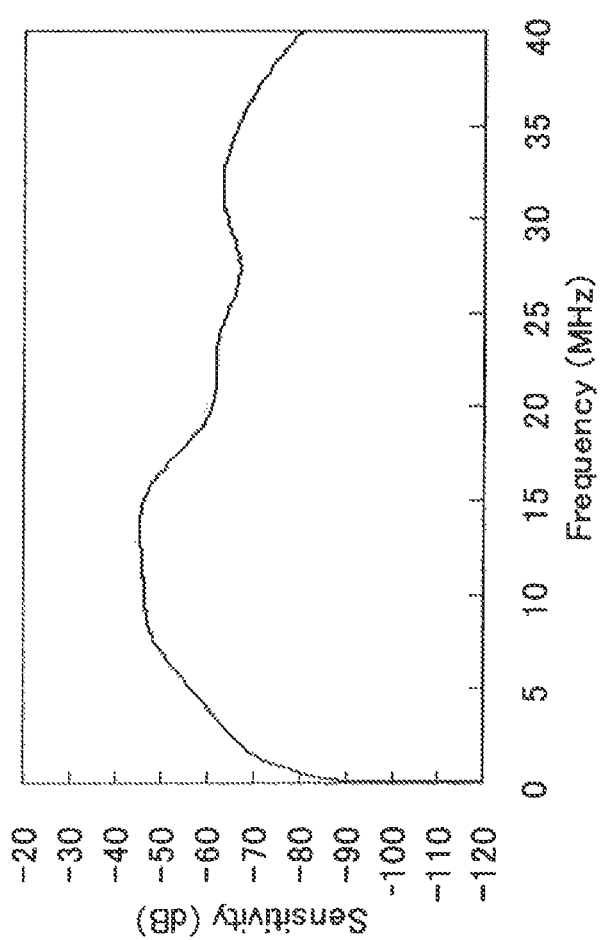
FIG.21

LAMINATED PIEZOELECTRIC BODY, LAMINATED PIEZOELECTRIC BODY MANUFACTURING METHOD, AND ULTRASOUND TRANSDUCER AND ULTRASOUND DIAGNOSTIC DEVICE USING LAMINATED PIEZOELECTRIC BODY

CROSS REFERENCE TO RELATED APPLICATION

This Application is a 371 of PCT/JP2011/001033 filed on Feb. 23, 2011 which, in turn, claimed the priority of Japanese Patent Application No. 2010-084018 filed on Mar. 31, 2010 and 2010-084533, filed Mar. 31, 2010, all applications are incorporated by reference herein.

TECHNICAL FIELD

The present invention is related to a laminated piezoelectric body formed by laminating piezoelectric bodies in a plurality of layers and a method of manufacturing the laminated piezoelectric body. In addition, the present invention relates to an ultrasound transducer using the laminated piezoelectric body which is suitably used as an Ultrasound probe of an ultrasound diagnostic device and the like, and an ultrasound diagnostic device using the laminated piezoelectric body.

BACKGROUND ART

Generally, a piezoelectric body is used in an ultrasound transducer. This is because a piezoelectric body has a so-called coupling effect between an electric system and a mechanical system for converting mechanical energy into electrical energy and, conversely, electrical energy into mechanical energy. The piezoelectric body has a sheet shape, a plate shape, or a rod shape and is provided with a pair of electrodes, one electrode being fixed to a rear layer and the other electrode being in contact with a medium via an acoustic lens or a matching layer.

Many piezoelectric ultrasound transducers emit sound waves toward a medium or detect sound waves propagating through the medium in a $d_{33}$ mode or an $e_{33}$ mode. It is generally considered that the $d_{33}$ mode is a longitudinal vibration of a column vibrator and that the $e_{33}$ mode is a thickness vibration of a plate vibrator. Ferroelectrics such as PZT ceramics and PVDF, high dielectrics such as P(VDCN/VAc), and porous polymer electret piezoelectric bodies exhibit the $d_{33}$ mode or the $e_{33}$ mode by retaining residual polarization due to an orientation of an electric dipole by polling processing. On the other hand, with piezoelectric crystals without residual polarization, a C axis in the case of piezoelectric crystals such as ZnO, LiNbO$_3$, and KNbO$_3$ and the A axis in the case of quartz are respectively oriented perpendicular to an electrode surface to exhibit the $d_{33}$ mode or the $e_{33}$ mode in the case of quartz, a $d_{11}$ mode or an $e_{11}$ mode). Piezocomposite materials are dependent on what materials are used.

With a piezoelectric body constituting an ultrasound transducer, a simplest mechanical boundary condition is a case where one end is a fixed end and the other end is a free end. In theory, an acoustic impedance Z (unit: MRayl.) and a boundary condition of an object in contact have a relationship in which Z=0 represents the free end and Z=∞ represents the fixed end. However, the present specification is not as strict, and with the exception of an adhesion layer and an electrode layer, a fixed end is assumed when an impedance Z of a piezoelectric material is smaller or equal to an impedance Z of an object in contact and a free end is assumed when the impedance Z of the piezoelectric material is greater. In addition, a resonance of a longitudinal vibration or a thickness vibration of a piezoelectric body is used by an ultrasound transducer to transmit and receive waves, and a resonance frequency fr thereof is determined primarily by physical properties and dimensions of the piezoelectric body and, to a lesser degree, by a structure of the transducer and how the transducer is pressed against a medium. Therefore, in the present specification, factors which alter the resonance frequency besides than dimensions and properties of a piezoelectric body are eliminated.

First, the resonance frequency fr in the $d_{33}$ mode or the $e_{33}$ mode of a piezoelectric body is given using a sound velocity v and a height (thickness) h of the piezoelectric body by Expression (1) below.

$$fr = v/4h \quad (1)$$

This is generally referred to as a resonance in a λ/4 resonance mode, λ denotes a wavelength inside the piezoelectric body. There is also a λ/2 resonance mode with both ends free. A resonance frequency thereof is double the resonance frequency of the λ/4 resonance mode.

Meanwhile, the sound velocity v of the piezoelectric body is given by Expression (2) below in the case of a longitudinal vibration of a column vibrator and by Expression (3) below in the case of a thickness vibration of a plate-like thickness vibrator.

$$v = (1/s\rho)^{1/2} \quad (2)$$

$$v = (c/\rho)^{1/2} \quad (3)$$

where s denotes elastic compliance, c denotes elastic stiffness, and ρ denotes density.

From Expressions (1) to (3) above, it is understood that respective frequencies of wave transmission and wave reception by a transducer are primarily determined by a height (thickness) h, an elastic modulus s, and a density ρ of a piezoelectric body.

Furthermore, for ultrasound diagnostic devices used in the fields of medicine, architecture, and the like, there are demands for higher frequencies and improved wave transmitting/receiving performances in transducers for the purpose of obtaining images with higher resolutions. In regards to improving a wave transmitting/receiving performance of an ultrasound transducer using a piezoelectric body, electrical impedance matching between the transducer and an electric processing circuit is an important factor in transmitting electrical signals at a high S/N ratio. In addition, in regards to achieving a higher frequency, since wave transmitting/receiving frequencies are determined by the thickness of a piezoelectric body, the piezoelectric body must be thinned. Although thinning of a piezoelectric body causes a decline in electrical impedance and is therefore beneficial in terms of impedance matching with an electrical circuit, a magnitude of decline is, at best, no more than an inverse of a thickness ratio. Furthermore, thinning of a piezoelectric body increases the difficulty of a production process in terms of film thickness control, handling, and the like.

Therefore, in conventional art, a harmonic component of a wave transmission/reception signal of a conventional λ/4 resonant transducer is used in order to obtain a high-frequency signal. However, since a harmonic component has a lower sensitivity than a fundamental wave component and is susceptible to attenuation due to damping by the piezoelectric body or surrounding materials, it is difficult to obtain a signal with a high S/N ratio. In consideration thereof, an $e_{33}$ thickness-stretch mode will be described with reference to FIG. 1 as an example of ultrasound wave transmission/reception using harmonics. FIG. 1 and the following description are presented in Non-Patent Document 1. Constants of the elements constituting an equivalent circuit shown in FIG. 1 are given in Expressions (4) to (6) below.

$$C_n = p_n k_t^2 C_0 \quad (4)$$

$$L = 1/\omega_{p1}^2 C_1 \quad (5)$$

and $$p_n = (1/n^2)(8/\pi^2), n = 2m-1 \quad (6)$$

where $C_n$ denotes a capacitance of each element, L denotes inductance, kt denotes an electromechanical coupling coefficient in the thickness-stretch mode, and $\omega_{p1}$ denotes resonance frequency.

By incorporating an approximation of $p_n \cong 1/n^2$ into Expression (6) above, Expression (4) becomes Expression (7) below.

$$C_n/C_0 = k_1^2/n^2 \quad (7)$$

Expression (7) indicates that an effective value of the electromechanical coupling coefficient in an n-th order harmonic decreases to 1/n, in the case of a first order mode, since n=1, Expression (7) becomes Expression (8) below.

$$C_n = 1/C_0 = k_t^2 \quad (8)$$

Expression (8) is consistent with an expression when incorporating substitutions of $\in^T = C_0 + C_n$ and $\in^S = C^0$ in a relational expression (9) between $k_t$ and permittivity in the first order mode.

$$\in^T/\in^S = 1 + k_t^2 \quad (9)$$

where $\in^S$ denotes permittivity under a clamped condition, $\in^T$ denotes permittivity under a free condition, and $C_0$ and $C_n$ denote capacitance. For the $d_{33}$ mode, a similar result is obtained by replacing Expression (4) with Expression (10) below.

$$C_n = p_n(k_{33}^2/1 - k_{33}^2)C_0 \quad (10)$$

In addition, an effective value of an electromechanical coupling coefficient when transmitting and receiving third order harmonics is given by Expression (7) in the case of n=3, and by letting an apparent coupling coefficient be $k_t'$, $k_t' = k_t/n = k_t/3$ is obtained. This result signifies that the apparent coupling coefficient attenuates to ⅓ when transmitting and receiving third order harmonics.

FIG. 2 is a graph showing frequency characteristics (calculated vales) of a complex permittivity of a piezoelectric body in which a first order mode of resonance in a thickness direction is represented by a frequency of 1 MHz. In FIG. 2, an abscissa represents frequency in units of MHz and an ordinate represents complex permittivity. However, $k_t$=0.3, h/2v=2.485×10⁻⁷(s), and tan $\delta_m$=0.04.

A local maximum and a local minimum of a real part (denoted by reference character α1) and a local maximum of an imaginary part (denoted by reference character α2) at 1 MHz are of the first order mode of resonance in the thickness direction. Subsequently, a third order harmonic component is observed at 3 MHz and a fifth order harmonic component is observed at 5 MHz. Meanwhile, as shown in FIG. 3, applying the third order harmonic component (dashed line) shown in FIG. 2 to a piezoelectric body model (solid line) with 3 MHz as a first order mode revealed that, by reducing a coupling coefficient and a piezoelectric body thickness of the piezoelectric body model to ⅓, a waveform of the piezoelectric body model becomes consistent with that of a piezoelectric body with 3 MHz as a third order mode. This result is consistent with the interpretation presented above. FIG. 3 is a graph showing frequency characteristics (calculated values) of a complex permittivity of a piezoelectric body exhibiting thickness vibration. In FIG. 3, an abscissa represents frequency in units of MHz and an ordinate represents complex permittivity. However, as described earlier, the dashed line represents $k_t$=0.3, h/2v=2.485×10⁻⁷(s), and tan $\delta_m$=0.04. On the other hand, the solid line represents $k_1$=0.1, h/2v=3.300× 10⁻⁷(s), and tan $\delta_m$=0.04.

As described above, with conventional art, an apparent electromechanical coupling coefficient decreases to 1/n while a harmonic is being detected and electrical impedance is primarily determined by dimensions of a piezoelectric body.

Meanwhile, with medical ultrasound diagnostic devices, harmonic imaging (THI) diagnostics of body tissue using a harmonic signal is becoming a standard diagnostic modality due to its ability to produce diagnostic images with clarity not possible with conventional B-mode diagnostics. Harmonic imaging technology has many advantages due to the use of higher frequencies including a reduced sidelobe level, increased SiN, enhanced contrast resolution, a thinner beam width, improved lateral resolution, lower sound pressure at short distances, and a lower likelihood of an occurrence of multiple reflections due to less fluctuation in sound pressure.

In consideration thereof, in Patent Document 1, signals received by respective piezoelectric elements of an ultrasound transducer are added in a phasing adder circuit and then commonly inputted to a fundamental wave band filter and a harmonic band filter. In addition, outputs thereof are weighted by gains respectively corresponding to a depth of a diagnosis domain of a subject and then combined. Patent Document 1 proposes an ultrasound diagnostic device which accordingly interpolates an attenuation of a harmonic component in a deep diagnosis domain with a fundamental wave. In other words, when receiving harmonics, the ultrasound diagnostic device disclosed in Patent Document 1 compensates for a reduction in the electromechanical coupling coefficient using a filter and an amplifier.

Similarly, in Patent Document 2, a harmonic piezoelectric element is laminated on a fundamental wave piezoelectric element, and a transmission ultrasound wave is emitted from the fundamental wave piezoelectric element. In addition, a fundamental wave signal component received by the fundamental wave piezoelectric element and a plurality of harmonic components received by the harmonic piezoelectric element are respectively passed through band separation filters to extract desired components, separately subjected to gain adjustment, and finally added together, Patent Document 2 proposes an ultrasound diagnostic device that accordingly obtains a signal in accordance with a depth of a diagnosis domain.

However, with the conventional art described above, filters and amplifiers must be inserted to signal paths from a large number of piezoelectric elements.

Furthermore, an organic material such as PVDF is more favorably used than an inorganic material such as PZT for receiving signals with a high frequency. However, while an inorganic material has high permittivity and therefore high capacitance and low electrical impedance and, as a result, matching with a subsequent stage circuit is relatively easy, an organic material has low permittivity and therefore low capacitance and high electrical impedance and, as a result, matching with a subsequent stage circuit is difficult.

Patent Document 1: Japanese Patent Application Publication No. 2002-11004
Patent Document 2: Japanese Patent Publication No. 4192598
Non-Patent Document 1: "Fundamentals of Piezoelectric Materials Science", Takuro Ishida, Ohmsha, Ltd.

SUMMARY OF THE INVENTION

The present invention has been made in consideration of the circumstances described above, and an object thereof is to provide a laminated piezoelectric body which is capable of increasing an output sound pressure during transmission or an output voltage during reception of a desired high-frequency component by an ultrasound transducer compared to those in a first order mode and which is capable of reducing electrical impedance, a laminated piezoelectric body manufacturing method, and an ultrasound transducer and an ultrasound diagnostic device that use the laminated piezoelectric body.

In a laminated piezoelectric body, a laminated piezoelectric body manufacturing method, an ultrasound transducer, and an ultrasound diagnostic device according to the present invention, a plurality of mutually laminated piezoelectric bodies are electrically connected in parallel to each other, and each of the plurality of piezoelectric bodies arranges an orientation of residual polarization or a crystal axis that is related to an electrical displacement or a sign of an electric field due to a direct piezoelectric effect in a direction which reduces sensitivity in a first resonance mode and increases sensitivity in a second resonance mode of a higher order than the first resonance mode with respect to an axis of a first-level piezoelectric body on a fixed end-side. As a result, the laminated piezoelectric body, the laminated piezoelectric body manufacturing method, the ultrasound transducer, and the ultrasound diagnostic device configured in this manner are capable of increasing an output sound pressure during transmission or an output voltage during reception of a desired high-frequency component compared to those in a first order mode and are capable of reducing electrical impedance.

These and other objects, features, and advantages of the present invention will become apparent from the following detailed description when considered in connection with the accompanying drawings.

BRIEF DESCRIPTION OF THE DRAWINGS

FIG. 7 is a diagram schematically showing displacement and distortion when n-th order harmonics are excited or detected by the n-layer piezoelectric transducer shown in FIG. 6.

FIG. 8 is a diagram showing a relationship between an orientation of residual polarization of each piezoelectric body or a C axis or an A axis of crystals when detecting n-th order harmonics and electrical displacement due to a direct piezoelectric effect in the laminated piezoelectric body shown in FIG. 7.

FIG. 9 is a diagram schematically showing a structure of a 2n-layer piezoelectric transducer for detecting an n-th order harmonic.

FIG. 10 is a sectional view schematically showing a structure of a two-layer piezoelectric transducer that is a detailed example of an embodiment conforming to the concept illustrated in FIG. 8.

FIG. 11 is a diagram for explaining displacement and distortion during harmonic transmission/reception by the two-layer piezoelectric transducer shown in FIG. 10.

FIG. 14 is a sectional view schematically showing a structure of a three-layer piezoelectric transducer that is another detailed example of an embodiment conforming to the concepts illustrated in FIGS. 8 and 5.

FIG. 15 is a diagram for explaining displacement and distortion during harmonic transmission/reception by the three-layer piezoelectric transducer shown in FIG. 14.

FIG. 18 is a graph showing experimental data and a simulation result of ultrasound wave transmitting/receiving performance of a comparative example of the three-layer piezoelectric body shown in FIG. 16.

FIG. 21 is a graph showing a simulation result regarding ultrasound wave transmitting/receiving performance of the six-layer piezoelectric body shown in FIG. 20.

DESCRIPTION OF EMBODIMENTS

Figure 1:
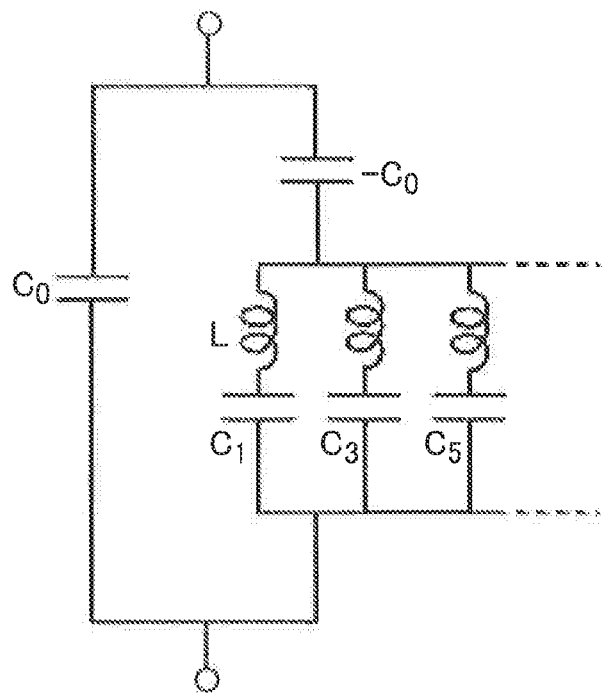
FIG. 1 is an equivalent circuit diagram in a thickness-stretch mode of a piezoelectric body.
Figure 2:
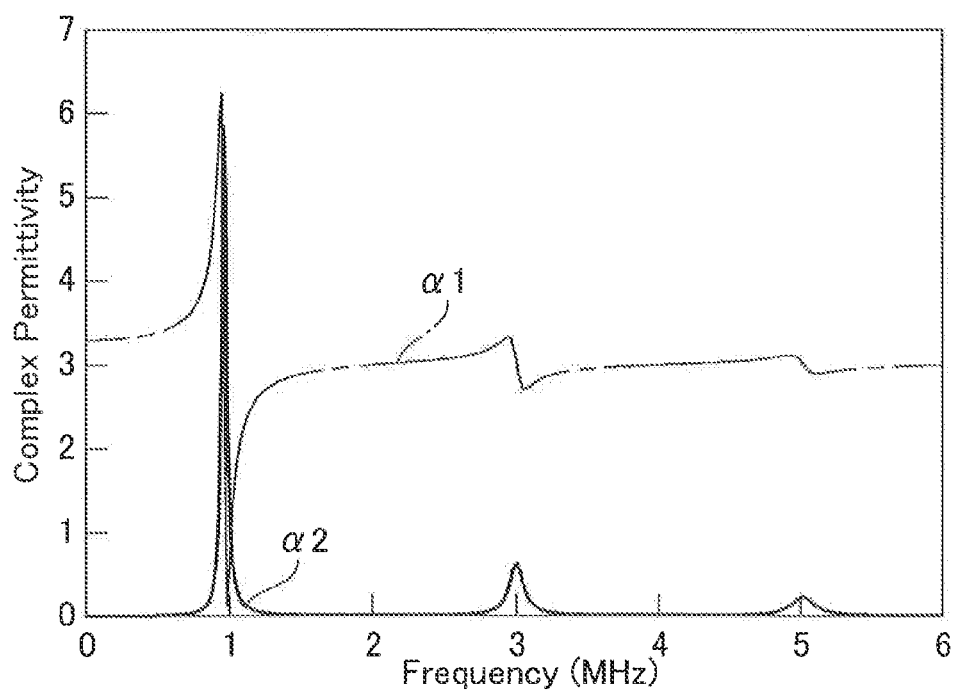
FIG. 2 is a graph showing frequency characteristics of complex permittivity of a piezoelectric body in which a first order mode of resonance in a thickness direction is represented by a frequency of 1 MHz.
Figure 3:
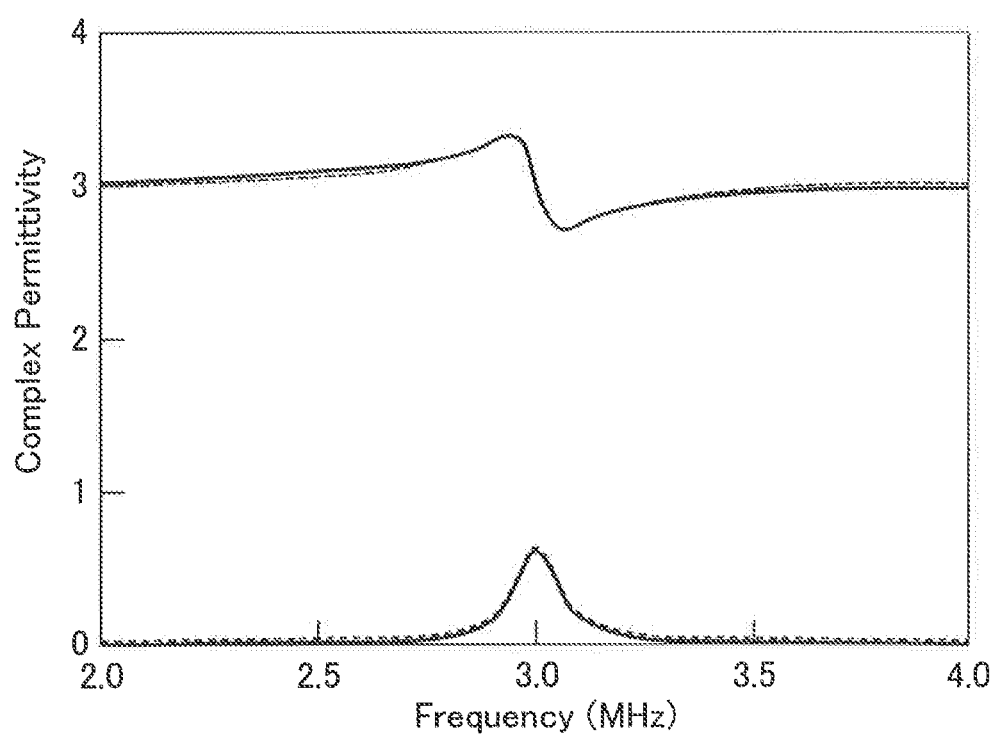
FIG. 3 is a graph showing frequency characteristics of complex permittivity of a third order mode of the piezoelectric body shown in FIG. 2 and a first order mode of a piezoelectric body in which a first order mode of resonance in a thickness direction is represented by a frequency of 3 MHz.

Hereinafter, an embodiment of the present invention will be described with reference to the drawings. In the respective drawings, like components are denoted by like reference characters and a description thereof will be omitted when appropriate.

(Fundamental Principle)

First, a fundamental principle of a laminated piezoelectric body, and an ultrasound transducer and an ultrasound diagnostic device (for example, a medical ultrasound diagnostic device) that use the laminated piezoelectric body will be described. The laminated piezoelectric body is constructed based on findings by the inventors of the present application that, by laminating piezoelectric bodies with equal thickness according to a predetermined rule, a component of a resonance mode of a high order and, in particular, a resonance mode of a third or higher order can be efficiently transmitted and received. Although many methods of laminating a plurality of piezoelectric bodies have already been reported, the present application focuses on a presence of a distortion distribution in a piezoelectric body when transmitting and receiving a component of a high order resonance mode and, in particular, a resonance mode of a third or higher order.

As an example, for the sake of convenience, a $\lambda/4$ vibrator shown in FIG. 4 in which three piezoelectric bodies A1, A2, and A3 are laminated will be described, where $\lambda$ denotes wavelength. With the $\lambda/4$ vibrator, in an excited state in a $\lambda/4$ resonance mode, it is assumed that the three piezoelectric bodies A1, A2, and A3 expand and contract in synchronization and perform an overall maximum expansion/contraction of $\Delta Z$. In addition, if $z_0$ denotes a coordinate of a back surface position on a first layer (first level) piezoelectric body A1 that is in contact with a fixed end or, in other words, a rear layer having an acoustic impedance that is smaller than 40 MRayl, but still sufficiently large, then a displacement of the position due to expansion/contraction is given as $z_0 = \Delta Z \sin 0° = 0$. In contrast, a displacement of a coordinate $z_1$ of a front surface position on the first layer piezoelectric body A1 is given as $z_1 = \Delta Z \sin 30° = 0.5\Delta Z$. A displacement of a coordinate $z_2$ of a front surface position on a second layer (second level) piezoelectric body A2 is given as $z_2 = \Delta Z \sin 60° = 0.87\Delta Z$. In addition, a front surface of a third layer (third level) piezoelectric body A3 is in contact with a free end or, in other words, a space having an acoustic impedance that is greater than 0 described above but still sufficiently small, and a displacement of a coordinate $z_3$ of a front surface position of the third layer piezoelectric body A3 is given as $z_3 = \Delta Z \sin 90° = 1.0\Delta Z$. Now, as far as the front and back sides of the piezoelectric bodies A1, A2, and A3 are concerned, upon pressurization of the piezoelectric bodies in a thickness direction (a lamination direction), a side on which a positive voltage is generated will be defined as front and a side on. Which a negative voltage is generated will be defined as back.

Figure 4:
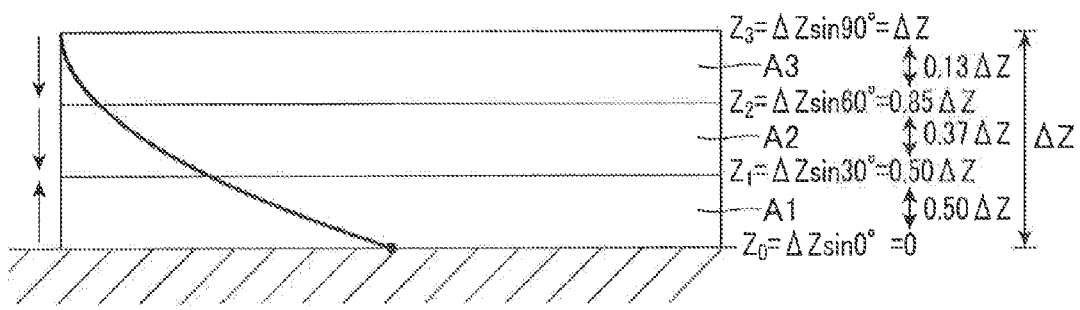
FIG. 4 is a schematic sectional view of a λ/4 resonance state in a three-layer piezoelectric transducer.

In other words, in the case of the three-layer piezoelectric bodies A1, A2, and A3 shown in FIG. 4, among the overall expansion/contraction $\Delta Z$, the fixed end-side piezoelectric body A1 is responsible for an expansion/contraction of $0.5\Delta Z$, the second layer piezoelectric body A2 is responsible for an expansion/contraction of $0.37\Delta Z$, and the third layer piezoelectric body A3 only expands/contracts by $0.13\Delta Z$. In this manner, with the laminated piezoelectric body, while the respective piezoelectric bodies A1, A2, and A3 expand/contract in synchronization (in a same direction) during a resonance of a fundamental wave in the $\lambda/4$ resonance mode, the respective piezoelectric bodies A1, A2, and A3 do not uniformly expand/contract by a same amount and have an inhomogeneous distortion distribution in which amounts of expansion/contraction differ from each other.

Figure 5:
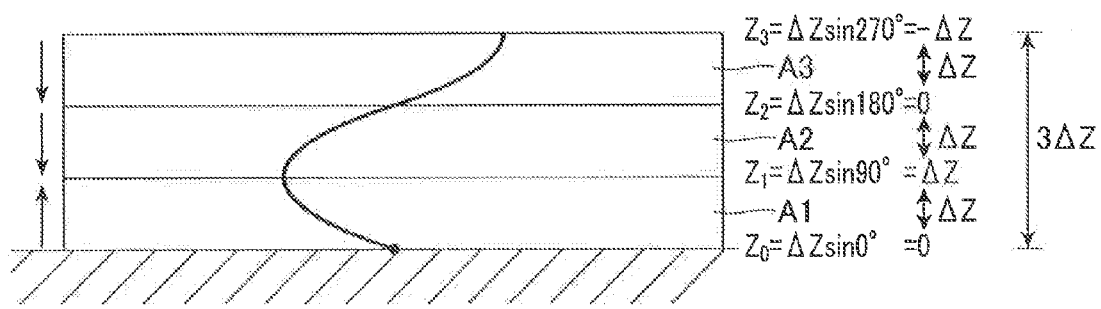
FIG. 5 is a schematic sectional view of a 3λ/4 resonance state in the three-layer piezoelectric transducer shown in FIG. 4.

On the other hand, a result of resonating a similar laminated piezoelectric body in a $3\lambda/4$ resonance mode is as shown in FIG. 5. Specifically, a coordinate $z_0$ of a back surface position on a first layer piezoelectric body A1 is given as $z_0 = \Delta Z \sin 0° = 0$, a coordinate $z_1$ of a front surface position on the first layer piezoelectric body A1 is given as $z_1 = \Delta Z \sin 90° = \Delta Z$, a coordinate $z_2$ of a front surface position on a second layer piezoelectric body A2 is given as $z_2 = \Delta Z \sin 180° = 0$, and a coordinate $z_1$ of a front surface position on a third layer piezoelectric body A3 is given as $z_3 = \Delta Z \sin 270° = -\Delta Z$. Therefore, in contrast to the first layer piezoelectric body A1 which expands by $\Delta Z$, the second layer and third layer piezoelectric bodies A2 and A3 respectively contract by $\Delta Z$.

In consideration thereof, the present inventors have focused on such an inhomogeneous distortion distribution and have laminated piezoelectric bodies at inconsistent locations (which correspond to a "−" sign) by reversing front and back sides of the piezoelectric bodies so that residual polarization ferroelectric such as PZT and PVD) of each piezoelectric body or an orientation of a C axis or an A axis (an axis that determines a sign of $d_{33}$, $e_{33}$, $d_{11}$, and $e_{11}$) of crystals (such as quartz) becomes consistent with an electrical displacement or a sign of an electric field in a distortion distribution during harmonic transmission/reception. In the case of FIGS. 4 and 5, as indicated by arrows on a left hand-side, second layer and third layer piezoelectric bodies A2 and A3 are laminated such that an orientation of the residual polarization or a crystal axis is opposite to that of the first layer piezoelectric body A1 Accordingly, with a laminated piezoelectric body configured as described above, a component of a fundamental wave $\lambda$ becomes $0.5 \cdot \Delta Z + 0.37 \cdot (-\Delta Z) + 0.13 \cdot (-\Delta Z) = 0$ and is eliminated, while a component of a third order harmonic $3\lambda$ becomes $1 - \Delta Z + (\sim 1) \cdot (\sim \Delta Z) + (\sim 1)) \cdot (\sim \Delta Z) = 3\Delta Z$ and can be extracted.

Next, with reference to FIG. 6, a case will be described in which an n-th order harmonic is transmitted and received by a $\lambda/4$ vibrator in which n-number (where n is an integer equal to or greater than 4) of piezoelectric bodies are laminated. In order to simplify the model, one end of a laminated film is fixed to a base (rear layer) and another end is set as a free end. Effects of an impedance matching layer and a rear layer (backing layer), a thickness of an adhesion layer, and the like are to be eliminated.

Figure 6:
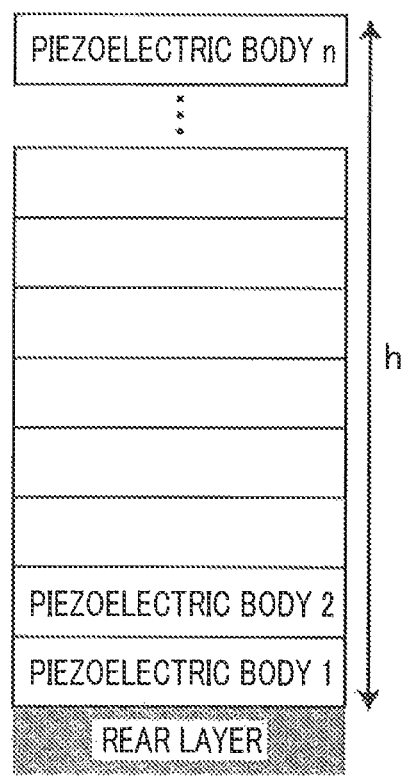
FIG. 6 is a schematic sectional view of an n-layer piezoelectric transducer.

FIG. 7 is a diagram schematically showing displacement and distortion when an n-th order harmonic is excited or detected by the n-layer piezoelectric transducer shown in FIG. 6. FIG. 7A represents a lamination condition, FIG. 7B shows displacements of the respective layers at a given moment, and FIG. 7C shows a polarity of distortions. In a similar manner to FIGS. 4 and 5 described earlier, an interfacial boundary between the base and a piezoelectric body in contact with the base is assumed to be an origin $z_0$ and coordinates in a height direction (a thickness direction, a lamination direction) of the elements are denoted by $z_1, z_2, z_3, \ldots, z_n$. Inside the laminated piezoelectric body, displacements of the respective piezoelectric body layers form a sine wave having an origin $z_0$ on a boundary between the rear layer and the first-level piezoelectric body 1.

Generally, it is known that when n-th harmonics ($n \geq 1$) are excited in a thickness direction, a displacement $\xi(z)$ at a height z is given by Expression (11) below (for example, reference: "Fundamental Physics Library Volume 8: Vibration and Undulation", Masataka Ariyarna, Shokabo Publishing Co., Ltd.).

$$\xi(z,t) = \xi_0 \sin(n\pi/2 \cdot z/h)(\cos n\omega_{ri} t + \theta) \quad (11)$$

where $\omega_r$ denotes a resonance frequency $2\pi f_r$ of the laminated piezoelectric body, and $\theta$ denotes a phase difference between stress and displacement when receiving voltage or a sound wave. A coefficient $\xi_0 \sin(n\pi/2 \cdot z/h)$ signifies an amplitude of a displacement at a height z. In the following description, time terms will be omitted.

In this case, a displacement $\xi(z_1)$ at a coordinate $z_1$ is given by Expression (12) below.

$$\xi(z_1) = \xi_0 \sin(n\pi/2 \cdot z/h) \quad (12)$$

Since a relationship between displacement $\xi(z)$ and distortion S is given by Expression (13) below a distortion $S_m$ of an m-th layer piezoelectric body is given by Expression (14) below, where m=1 to n, and $z_0=0$.

$$dS = d\xi/dz \quad (13)$$

$$S_m = [\xi(z_m) - \xi(z_{m-1})]/(z_m - z_{m-1}) \quad (14)$$

Therefore, the distortion $S_1$ of the piezoelectric body 1 is given by Expression (15) below.

$$S_1 = \Delta h_1/h_1 = \xi_0 \sin(n\pi/2 \cdot h_1/h)/h_1 \quad (15)$$

where $\Delta h_1$ denotes a variation in thickness of the piezoelectric body 1, $\xi(z_1) - \xi(z=0)$, and $h_1$ denotes the thickness of the piezoelectric body 1. Similarly, in regards to the piezoelectric body 2, a distortion $S_2$ is given by Expression (16) below.

$$S_2 = \Delta h_2/h_2 = \xi_0 \{\sin(n\pi/2 \cdot (h_1+h_2)/h) - \sin(n\pi/2 \cdot h_1/H)\}/h_2 \quad (16)$$

A distortion $S_m$ of an m-th layer piezoelectric body is given by (17) below.

$$S_m = \Delta h_m/h_m = \xi_0 \{\sin(n\pi/2 \cdot z_m/h) - \sin(n\pi/2 \cdot z_{m-1}/h)\}/h_m \quad (17)$$

Expression (17) signifies that a distortion of a piezoelectric body at the m-th layer is determined by $\sin(np/2 \cdot z_m/h) - \sin(np/2 \cdot z_{m-1}/h)$ and does not uniformly expand/contract as described above. Therefore, it is understood that by reversing the front and back sides between a piezoelectric body for which the term described above has a positive sign and a piezoelectric body for which the term described above has a negative sign, an electrical displacement or a sign of an electric field due to a direct piezoelectric effect can be matched between the piezoelectric bodies and an electrical signal of n-th order harmonics of a piezoelectric element can be obtained in an efficient manner.

Furthermore, by equalizing thicknesses of the respective piezoelectric bodies, simplification is achieved as given in Expression (18) below.

$$z_m = (m/n)h, z_{m-1} = (m-1/n)h, h_m = h/m \quad (18)$$

By substituting Expression (18) into Expression (17), we get Expression (19) below.

$$S_m = m\xi_0 \{\sin(m\pi/2) - \sin[(m-1)\pi/2]\}/h \quad (19)$$

Next, an electric system will be considered. An electrical displacement (a charge per unit electrode area) $D_m$ generated by an m-th layer piezoelectric body due to a direct piezoelectric effect is given by Expression (20) below.

$$D_m = e_{33} S_m \text{ or } D_m = d_{33} S_m = d_{33} T_m \quad (20)$$

where s denotes an elastic compliance of a piezoelectric body, in a case where respective piezoelectric bodies are electrically coupled in parallel to each other, a net electrical displacement $D_{Total}$ outputted by a laminated piezoelectric body is given by Expression (21) below, where $\Sigma$ in Expression (21) denotes a sum that ranges from m=1 to m=n.

$$d_{Total} = \Sigma D_m \quad (21)$$

If C denotes a capacitance of each piezoelectric body, then a capacity of the laminated piezoelectric body is given as $n \times C$ and electrical impedance decreases to 1/n of one piezoelectric layer.

Furthermore, based on Expressions (19) and (21) above, the inventors of the present application have discovered a regularity regarding a realization of a simple parallel coupling and regarding residual polarization or an arrangement of the C axis or the A axis of crystals at which a net electrical displacement outputted from a laminated piezoelectric body reaches maximum. In addition, the inventors of the present application have discovered that, when the number of laminations n is 4 or more, by matching the number of laminations n and the order of harmonics with each other, nodes and antinodes of an elastic wave propagating within a piezoelectric body can be matched with an interfacial boundary of the piezoelectric body, in which case distortions of respective piezoelectric bodies assume absolute values that are unchanged and phases that are inverted by 180 degrees, and n-th order harmonics can be detected with greater efficiency. More specifically, for example, in the case of FIG. 7 in which respective piezoelectric bodies are connected in series, if it is assumed that a first-level piezoelectric body 1 has a "+" distortion, a periodicity of "+, −, −, +" can be observed every four layers. A more theoretical explanation of the above will be given below.

FIG. 8 shows an example of a relationship between an orientation of residual polarization of each piezoelectric body or a C axis or an A axis of crystals when detecting an n-th order harmonic and electrical displacement D (C/m²) due to a direct piezoelectric effect in an n-layer piezoelectric body. Electrodes are provided at interlayers between the respective piezoelectric bodies of the n-layer piezoelectric body and on surfaces of piezoelectric bodies at both ends of the n-layer piezoelectric body, and farther-side electrodes of mutually adjacent piezoelectric bodies are coupled by connecting wirings to connect the respective piezoelectric bodies in parallel. In addition, residual polarization (in the case of a piezoelectric body without residual polarization, a C axis of crystals (an A axis in case of quartz)) is oriented in a z axis direction. In the drawings, for the sake of convenience, a direction of the residual polarization or the C axis or the A axis of crystals of the piezoelectric body 1 is denoted as +P. This is done to distinguish whether the residual polarization or the C axis or the A axis of other crystals of other piezoelectric bodies are in the same direction or an opposite direction to that of the piezoelectric body 1, and is not intended to limit the polarization direction of the piezoelectric body 1.

As shown in FIG. 7C, distortions of the respective piezoelectric bodies have periodicity (in the case of FIG. 7C, the respective piezoelectric bodies are in series as described earlier). Therefore, when the orientations of residual polarization or the C axes or A axes of crystals are set so as to be parallel to each other, in order to achieve a high charge output or a high potential output, each electrode must be electrically insulated and independently wired, which is difficult in terms of structure and production.

However, in the present embodiment, as shown in FIG. 8, by performing parallel connection such that a periodicity of "+P, +P, −P, −P" is given to the residual polarization or the C axes or A axes of crystals of piezoelectric bodies every four layers or, in other words, with respect to an axis of a first-level piezoelectric body that is in contact with a rear layer, arranging a second-level piezoelectric body that is in contact with the first-level piezoelectric body in a same direction, arranging a third-level piezoelectric body that is in contact with the second-level piezoelectric body and a fourth-level piezoelectric body on top of the third-level piezoelectric body in opposite directions, and arranging subsequent piezoelectric bodies so as to have a periodicity of a same direction, a same direction, an opposite direction, and an opposite direction every four layers, electrical impedance can be reduced to 1/n of a single-layer piezoelectric body and, at the same time, a charge sensitivity between both terminals can be readily amplified n-fold.

Although a case of detecting an n-th order harmonic has been exemplified above, even in a reverse situation of transmitting an n-th order harmonic, efficiency may be improved compared to what is conventional by connecting an oscillator between terminals in FIG. 8. In the case of wave transmission, a relationship between distortion S and an applied electric field E is given by Expression (22) below.

$$S = dE \text{ or } S = (e/c)E \quad (22)$$

By connecting a voltage generator between both terminals of the laminated piezoelectric body shown in FIG. 8 and applying a voltage with a frequency corresponding to an n-th order harmonic, a distortion shown in FIG. 8 and a displacement shown in FIG. 7B are created and ultrasound waves may be excited within a medium. In addition, due to the relationship of electrical impedance described earlier, such a structure is capable of driving a high current at a low voltage.

On the other hand, FIG. 9 is a diagram schematically showing a structure of a 2n-layer piezoelectric transducer for detecting an n-th order harmonic. FIG. 9A represents a lamination condition, FIG. 9B shows displacements of the respective layers at a given moment, and FIGS. 9C and 9D respectively show coefficients of distortion and electrical displacement. The coefficients 0.3 and 0.7 represent respective relative ratios of distortion and electrical displacement and do not indicate absolute values. Moreover, an approximation of $\frac{1}{2}^{1/2} \cong 0.7$ is adopted. Electrodes are provided at interlayers between respective piezoelectric bodies and on both end surfaces of the piezoelectric bodies, and farther-side electrodes of mutually adjacent piezoelectric bodies are connected to each other in order to couple the respective piezoelectric bodies in parallel. In this case, compared to the n-layer piezoelectric transducer described earlier, while an electrical displacement due to a direct piezoelectric effect is the same, capacitance is doubled while electrical impedance is reduced by half. An arrangement of residual polarization or C axes or A axes repeats a pattern of "+P, −P, −P, +P, −P, +P, +P, −P" every eight layers with respect to a first-level piezoelectric body that is in contact with a rear layer.

A distortion $Sm^{n\omega}$ of each piezoelectric body is given by Expression (23) below, where m=1, 2, ... 2 n.

$$Sm^{n\omega} = 2n\xi_0^{n\omega}\{\sin[m(\pi/4)] - \sin[(m-1)(\pi/4)]\}/h \quad (23)$$

First Embodiment

Hereinafter, a first embodiment based on the concepts presented above will be described. First, as a first embodiment, detection of a 3λ/4 harmonic by a two-layer piezoelectric transducer shown in FIG. 10 will be described. A structure of a two-layer piezoelectric transducer is the simplest among laminated piezoelectric bodies. In this case, the order of a harmonic used for wave transmission/reception and the number of laminations are inconsistent. However, by applying the concepts described above as follows, an efficiency of wave transmission/reception can be improved.

Specifically, distortions $S_1$ and $S_2$ of a piezoelectric body 1 and a piezoelectric body 2 shown in FIG. 10 are respectively given by Expression (24) and Expression (25) below.

$$S_1 = \Delta h_1/h_1 = \xi_0 \sin(n\pi/2 \cdot h_1/h)/h_1 \quad (24)$$

$$S_2 = \Delta h_2/h_2 = \xi_0\{\sin(n\pi/2) - \sin(n\pi/2 \cdot h_1/h)\}/h_2 \quad (25)$$

where h denotes a height of a laminated piezoelectric body, and $h_1$ and $h_2$ denote heights of the respective piezoelectric bodies and have a relationship expressed as $h_1 = h_2 = h/2$.

A response to 3λ/4 resonant harmonics is given by n=3. Distortions $S_1^{3\omega}$ and $S_2^{3\omega}$ in this case are given by Expression (26) and Expression (27) below.

$$S_1^{3\omega} = 2\xi_0^{3\omega}\sin(3\pi/4)/h = 2(\xi_0^{3\omega}/2^{1/2})/h \quad (26)$$

$$S_2^{3\omega} = 2\xi_0^{3\omega}\{\sin(3\pi/2) - \sin(3\pi/4)\}/h = -2\xi_0^{3\omega}(1+1/2^{1/2})/h \quad (27)$$

where the superscript 3ω denotes a displacement of third order harmonies. Now, by adopting an approximation of $\frac{1}{2}^{1/2} \cong 0.7$, the respective expressions indicate that the distortion of the piezoelectric body 2 and the distortion of the piezoelectric body 1 have an amplitude ratio of −1.7:+0.7 in the case of third order harmonics.

Displacements and signs of distortions of the respective piezoelectric bodies are shown in FIG. 11. FIG. 11A shows displacement and FIG. 11B shows distortion. A distortion ratio of the piezoelectric body 1 and the piezoelectric body 2 is as shown in FIG. 11B. Absolute values of distortions of the respective piezoelectric bodies are inconsistent because boundaries of the respective piezoelectric bodies are not consistent with nodes and antipodes of the displacements.

Figure 12:
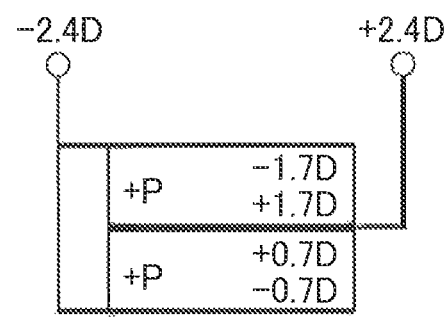
FIG. 12 is a diagram showing a relationship between an orientation of residual polarization of each piezoelectric body when detecting a third-order harmonic and electrical displacement due to a direct piezoelectric effect in the laminated piezoelectric bodies shown in FIGS. 10 and 11.

Therefore, as shown in FIG. 12, when electrodes on farther-side surfaces of mutually adjacent piezoelectric bodies are connected to each other in order to couple the respective piezoelectric bodies in parallel, the electrical impedance of the laminated piezoelectric body becomes ½ of an impedance of a single piezoelectric body. Furthermore, when an orientation of residual polarization or an orientation of a C axis or an A axis of crystals of the piezoelectric body 1 is set in the same direction as an orientation thereof in the piezoelectric body 2, an electrical displacement $D_{1,-1}^{3\omega}$ due to a direct piezoelectric effect is added with a polarity of one of the piezoelectric bodies reversed by the parallel connection, and are given by Expression (28) below.

$$D_{1,-1}^{3\omega} = 2(1+2^{1/2})e\xi_0^{3\omega}/h \quad (28)$$

Meanwhile, a response to a fundamental wave can be understood as a case of n=1 in Expressions (24) and (25). In other words, distortions $S_1^{\omega}$ and $S_2^{\omega}$ are given by Expression (29) and Expression (30) below.

$$S_1^{\omega} = 2\xi_0^{\omega}\sin(\pi/4)/h = 2(\xi_0^{\omega}/2^{1/2})/h \quad (29)$$

$$S_2^{\omega} = 2\xi_0^{\omega}\{\sin(\pi/2) - \sin(\pi/4)\}/h = 2\xi_0^{\omega}\{1 - 1/2^{1/2}\}/h \quad (30)$$

Now, when performing a parallel coupling such as that shown in FIG. 12 and orienting residual polarization or C axes or A axes of crystals in a same direction, an electrical displacement $D_{1,1}^{\omega}$ is given by Expression (31) below.

$$D_{1,1}^{\omega} = 2e\xi_0^{\omega}(2^{1/2} - 1)/h \quad (31)$$

where 1 in the subscript corresponds to an orientation of the residual polarization or an orientation of the C axis or the A axis of crystals of each piezoelectric body and, starting from the left, indicate the orientation of the residual polarization or the orientation of the C axis or the A axis of crystals of piezoelectric body 1 and the orientation of the residual polarization or the orientation of the C axis or the A axis of crystals of piezoelectric body 2.

From the results described above, by taking distortion of each piezoelectric body into consideration and, in the case of a parallel connection, orienting the residual polarization or the C axes or the A axes of crystals in the same direction, a two-layer piezoelectric body structured as described above is capable of amplifying sensitivity by a factor of 2.4 with respect to a $3\lambda/4$ wave and reducing sensitivity by a factor of 0.4 with respect to a 2.14 wave. Therefore, by applying the concepts described above to an ultrasound transducer constituted by a two-layer piezoelectric body, signals in the $3\lambda/4$ resonance mode can be transmitted and received at a high S/N ratio.

Figure 13A:
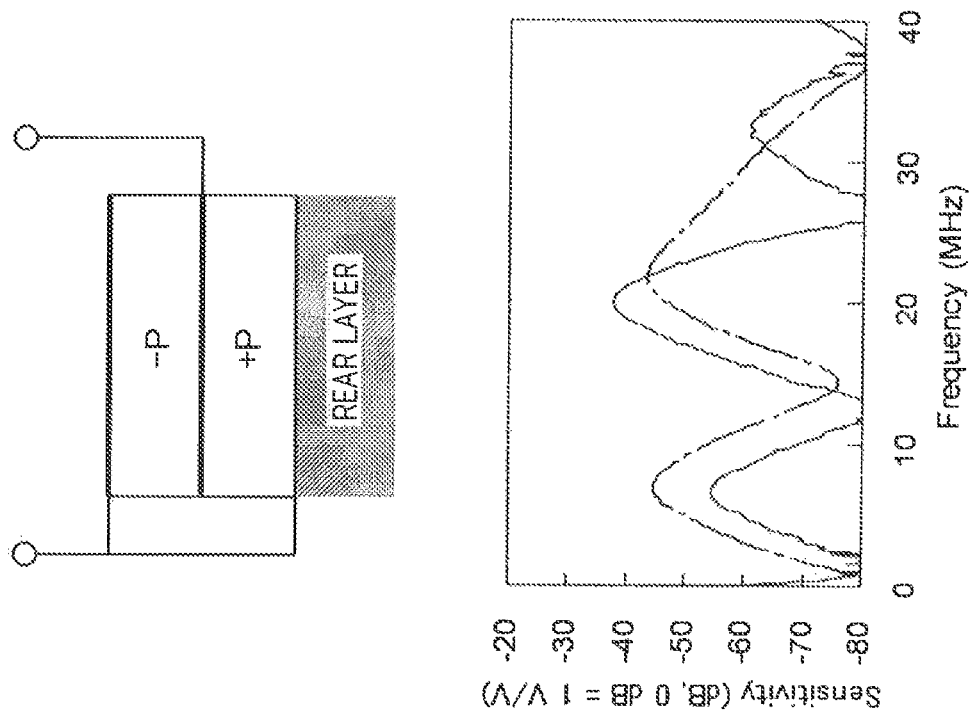
FIG. 13 is a graph showing experimental data and simulation results of ultrasound wave transmitting/receiving performance of the two-layer piezoelectric body shown in FIG. 10 and a comparative example thereof.
Figure 13B:
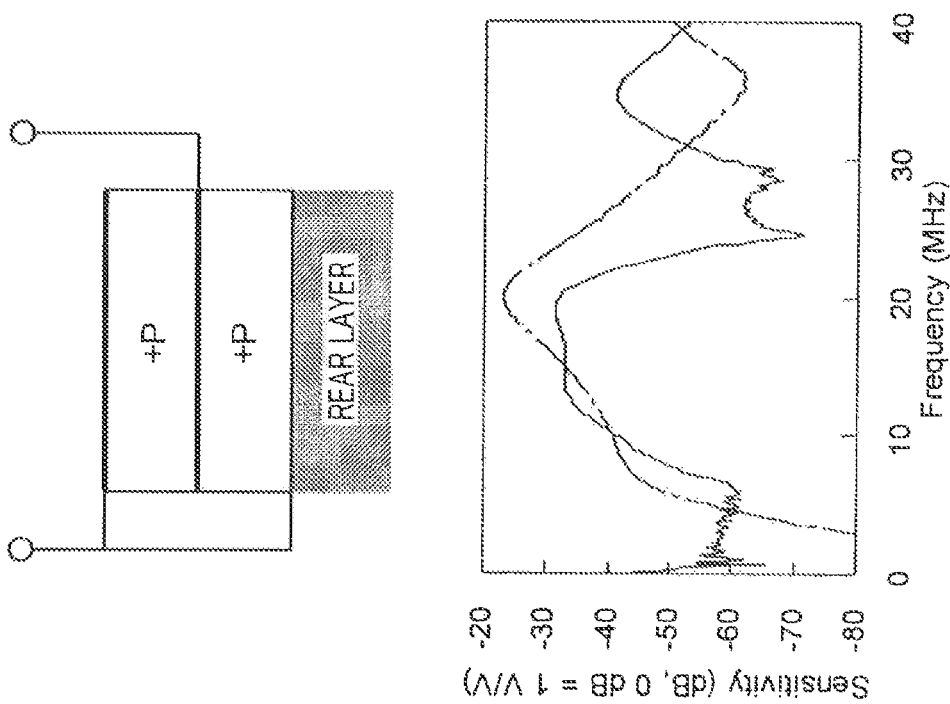

FIG. 13 shows results of an experiment and a simulation regarding wave transmission/reception sensitivity characteristics of an ultrasound transducer constituted by a two-layer piezoelectric body using P(VDF/TrFE). In FIG. 13A, an abscissa represents frequency in units of MHz and an ordinate represents sensitivity in units of dB. A solid line depicts an experiment result and a dashed line depicts a simulation result. In both cases, farther-side surfaces or, in other words, electrode surfaces formed on outer surfaces of mutually adjacent piezoelectric bodies are connected to each other in order to couple the respective piezoelectric bodies in parallel. In addition, a $\lambda/4$ resonance frequency is approximately 7 MHz and a $3\lambda/4$ resonance frequency is approximately 20 MHz. FIG. 13A shows a result in a case where polarizations are oriented in a same direction based on the concepts described above, and FIG. 13B shows a result in a case where polarizations are oriented in opposite directions for reference. As shown in FIG. 13A, when the polarization direction and wiring method based on the concepts described above are combined, a resonance peak in the $3\lambda/4$ resonance mode that is observed at 20 MHz is higher than a resonance peak in the $\lambda/4$ resonance mode that is observed at 7 MHz. In addition, compared to the result shown in FIG. 13B, the $3\lambda/4$ resonant peak has increased by 20 dB. As shown, even in the case of a two-layer piezoelectric body, by combining a polarization direction and a wiring method based on the concepts described above, a third order harmonic component can be increased and, at the same time, a fundamental wave component can be attenuated.

Second Embodiment

Next, detection of a third order harmonic by a three-layer piezoelectric transducer will be described. FIG. 14 is a diagram showing a schematic structure thereof. This three-layer piezoelectric transducer is also a $\lambda/4$ vibrator with one end of a laminated piezoelectric body fixed to a rear layer and the other end thereof being a free end.

First, a design process based on the concepts presented above will be described. As described earlier, a boundary between a rear layer (for example, a substrate) and a piezoelectric body 1 is assumed to be an origin $z_0$, and a coordinate of en element in a height direction (thickness direction, lamination direction) is denoted by z. Next, a distortion S created by each piezoelectric body is considered. Starting from a base side, it is assumed that piezoelectric bodies are laminated in an order of the piezoelectric body 1, a piezoelectric body 2, and a piezoelectric body 3. The coordinate z is assumed to be z=0 at the boundary between the substrate and the piezoelectric body 1, $z_1$ at a boundary between the piezoelectric body 1 and the piezoelectric body 2, $z_2$ at a boundary between the piezoelectric body 2 and the piezoelectric body 3, and $z_3$ at an end of the piezoelectric body 3. In addition, it is assumed that the piezoelectric body 1 has a thickness of $h_1$, the piezoelectric body 2 has a thickness of $h_2$, and the piezoelectric body 3 has a thickness of $h_3$.

In this case, since a displacement $\xi(z_1)$ at the coordinate $z_1$ is given by Expression (32) below, a distortion $S_1$ of the piezoelectric body 1 is given by Expression (33) below.

$$\xi(z_1)=\xi_0 \sin(n\pi/2 \cdot z_1/h) \tag{32}$$

$$S_1=\Delta h_1/h_1=\xi_0 \sin(n\pi/2 \cdot h_1/h)/h_1 \tag{33}$$

Similarly, respective distortions $S_2$ and $S_3$ of the piezoelectric body 2 and the piezoelectric body 3 are respectively given by Expression (34) and Expression (35) below.

$$S_2=\Delta h_2/h_2=\xi_0\{\sin(n\pi/2 \cdot (h_1+h_2)/h)-\sin(n\pi/2 \cdot h_1/h)\}/h_2 \tag{34}$$

$$S_3=\Delta h_3/h_3=\xi_0\{\sin(n\pi/2)-\sin(n\pi/2 \cdot (h_1+h_2)/h)\}/h_3 \tag{35}$$

In addition, distortions of the respective piezoelectric bodies during a resonance in a $3\lambda/4$ resonance mode are given by n=3 in Expressions (33) to (35) above. In a case where the respective piezoelectric bodies have a same thickness or, in other words, when $h_1=h_2=h_3$ h/3 in the expressions above, distortions $S_1^{3\omega}$, $S_2^{3\omega}$, and $S_3^{3\omega}$ of the piezoelectric bodies are respectively given by Expressions (36) to (38) below.

$$S_1^{3\omega}=\Delta h_1^{3\omega}/h_1=3\xi_0^{3\omega}\sin(\pi/2)/h=3\xi_0^{3\omega}/h \tag{36}$$

$$S_2^{3\omega}=\Delta h_2^{3\omega}/h_2=3\xi_0^{3\omega}\{\sin(\pi)-(\pi/2)\}/h=-3\xi_0^{3\omega}/h \tag{37}$$

$$S_3^{3\omega}=\Delta h_3^{3\omega}/h_3=3\xi_0^{3\omega}\{\sin(3\pi/2)-\sin(\pi)\}/h=-3\xi_0^{3\omega}/h \tag{38}$$

where the superscript $3\omega$ signifies a response of third order harmonics. These expressions show that, in a resonance in the $3\lambda/4$ resonance mode, the distortions of the piezoelectric body 2 and the piezoelectric body 3 and the distortion of the piezoelectric body 1 have opposite phases.

FIG. 15 is a diagram showing displacements and signs of distortions of the respective piezoelectric bodies. FIG. 15A shows displacement and FIG. 15B shows distortion. Since the laminated piezoelectric body according to the present embodiment transmits and receives third order harmonics and is a lamination of three piezoelectric bodies, as shown in FIG. 15A and in FIG. 5 described earlier, nodes and antinodes of displacements are consistent with boundaries between the respective piezoelectric bodies, in this case, as far as the distortions of the respective piezoelectric bodies are concerned, if the distortion of the piezoelectric body 1 is assumed to be "+", then distortions of the piezoelectric body 2 and the piezoelectric body 3 are "−" as shown in FIG. 15B and in FIG. 5 described earlier.

Figure 16:
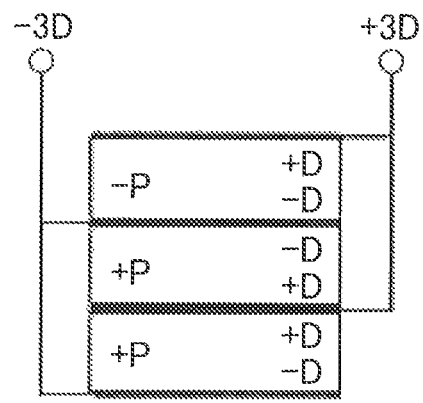
FIG. 16 is a diagram showing a relationship between an orientation of residual polarization of each piezoelectric body when detecting a third-order harmonic and electrical displacement due to a direct piezoelectric effect in the laminated piezoelectric bodies shown in FIGS. 14 and 15.

The derivation of an optimal structure of an electrical system based on the behavior of the dynamic system presented above will now be described. As shown in FIG. 16, by connecting electrodes on farther-side surfaces of mutually adjacent piezoelectric bodies to each other, and extracting wirings from the electrodes and coupling the wirings, the respective piezoelectric bodies can easily be electrically connected to each other in parallel. In this case, an electrical impedance of the laminated piezoelectric body decreases to ⅓ of a single piezoelectric body. In addition, with respect to an orientation of residual polarization or an orientation of a C axis or an A axis of crystals of the first-level piezoelectric body 1 (+P), an orientation of residual polarization or an orientation of a C axis or an A axis of crystals of the second-level piezoelectric body 2 is set in a same direction (+P), and an orientation of a C axis or an A axis of crystals of the third-level piezoelectric body 3 is set in an opposite direction (−P). Due to such a configuration, a charge induced in the wiring is equal to a sum of charges generated by a direct piezoelectric effect. In this case, an electrical displacement $D_{1,1,-1}^{3\omega}$ induced between both terminals is given by Expression (39) below.

$$D_{1,1,-1}^{3\omega}=eS_1-e(S_2+S_3)=9e\xi_0^{3\omega}/h \tag{39}$$

where 1 and −1 in the subscript each corresponds to an orientation of the residual polarization or an orientation of the C axis or the A axis of crystals of each piezoelectric body and, starting from the left, indicate the orientation of the residual polarization or the orientation of the C axis or the A axis of crystals of piezoelectric body 1, the orientation of the residual polarization or the orientation of the C axis or the A axis of crystals of piezoelectric body 2, and the orientation of the residual polarization or the orientation of the C axis or the A axis of crystals of piezoelectric body 3.

In addition, a response to a λ/4 resonance is given by n=1, while distortions $S_1$, $S_2$ and $S_3$ of the respective piezoelectric bodies are respectively given by Expression (40), Expression (41), and Expression (42) below and have a relationship given by Expression (43) below.

$$S_1=\Delta h_1/h_1=3\xi_0 \sin(\pi/6)/h \tag{40}$$

$$S_2=\Delta h_2/h_2=3\xi_0\{\sin(\pi/3)-\sin(\pi/6)\}/h \tag{41}$$

$$S_3=\Delta h_3/h_3=3\xi_0\{\sin(\pi/2)-\sin(\pi/3)\}/h \tag{42}$$

$$S_1=S_2+S_3 \tag{43}$$

Meanwhile, in the parallel connection shown in FIG. 16, an electrical displacement $D_{1,1,-1}^{\omega}$ with respect to a resonance in a λ/4 resonance mode is given by Expression (44) below, which indicates that with a transducer formed by a three-layer piezoelectric body according to the present embodiment, the sensitivity based on a resonance in the λ/4 resonant mode is canceled.

$$D_{1,1,-1}^{\omega}=e(S_1+S_2+S_3)=0 \tag{44}$$

As a comparison, transmission/reception of third order harmonics by a three-layer piezoelectric body in which residual polarizations or C axes or A axes of crystals are simply arranged parallel to each other will be described below. An electrical displacement $D_{1,1,1}^{3\omega}$ created due to a direct piezoelectric effect by an laminated piezoelectric body in a 3λ/4 resonance is given by $$D_{1,1,1}^{3\omega}=e(S_1+S_2+S_3)=-3e\xi_0^{3\omega}/h \tag{45}$$

Therefore, in the present embodiment, as shown in Expression (45) above, an electrical displacement between terminals in a parallel connection can be improved three-fold (by approximately 10 dB).

Figure 17:
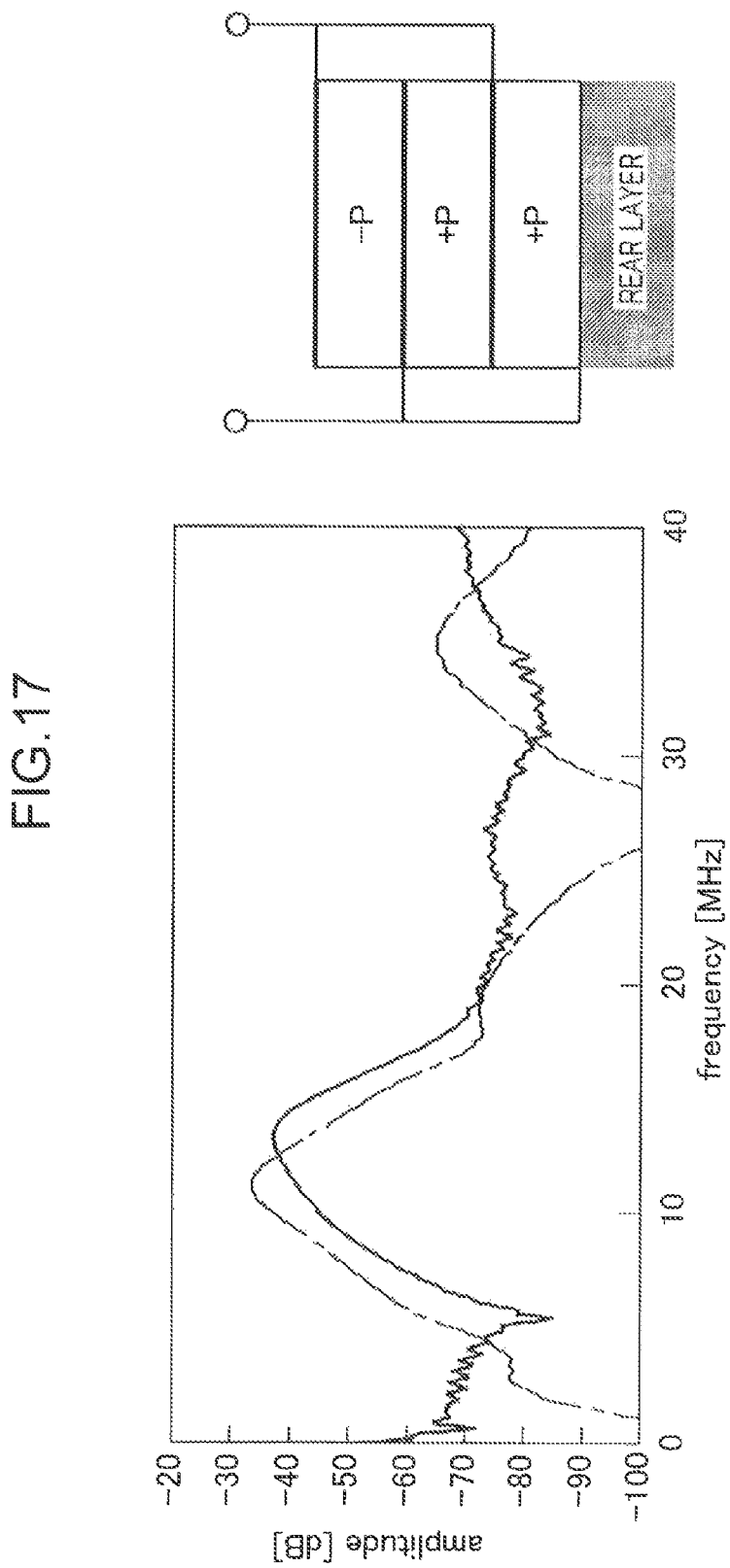
FIG. 17 is a graph showing experimental data and a simulation result of ultrasound wave transmitting/receiving performance of the three-layer piezoelectric body shown in FIG. 16.

FIG. 17 shows experimental data and a simulation result of ultrasound wave transmission/reception characteristics of the three-layer piezoelectric body shown in FIG. 16. For the experiment, a copolymer of vinylidene fluoride and trifluoroethylene (P(VDF/TrFE)) which is a typical ferroelectric polymer was used. A schematic structure of an ultrasound transducer is shown in the right hand-side diagram of FIG. 17. In this example, based on the concepts described above, a three-layer piezoelectric body is electrically coupled in series and a same orientation of polarization as that shown in FIG. 15 is adopted. The three-layer piezoelectric body has a height of approximately 120 μm and a resonance frequency in a λ/4 resonance mode is 4.5 MHz. In the left hand-side diagram, a solid line represents an experiment result and a dashed line represents a simulation result.

With reference to FIG. 17, at and below 20 MHz, both the experiment and the simulation do not exhibit peaks near 4.5 MHz corresponding to the resonance frequency and a resonance peak in the λ/4 resonance mode has disappeared. Therefore, a first peak of the transducer according to the present embodiment occurs at 13.5 MHz which is a resonance frequency of a 3λ/4 resonance mode of the transducer.

As a comparative example, a laminated piezoelectric body in which orientations of residual polarization of the piezoelectric body 2 and the piezoelectric body 3 have been set opposite to FIG. 17 is shown in a right hand-side diagram in FIG. 18. FIG. 18 also shows characteristics of the laminated piezoelectric body. As shown in a left hand-side diagram, the three-layer piezoelectric body exhibits peaks at 4.5 MHz which is a resonance frequency in a λ/4 resonance mode and at 13.5 MHz which is a third order harmonic component thereof. In addition, a sensitivity of the third order harmonic component is around −50 to −60 dB which is approximately 10 to 20 dB lower than the results of the present embodiment shown in FIG. 17. These experiment results also show that by combining a polarization direction and a wiring method based on the concepts described above, a third order harmonic component can be increased and a fundamental wave component can be attenuated.

While a method of transmitting and receiving third order harmonics using a three-layer piezoelectric body has been described above in the second embodiment, by matching the order of harmonics and the number of laminations in a laminated piezoelectric body, (i) conforming an interfacial boundary of a piezoelectric body with nodes and antinodes of an elastic wave of the piezoelectric body and coding a vibrational mode of each piezoelectric body, and based on the coding and a wiring method, (ii) orienting a residual polarization or a C axis or an A axis of crystals of each piezoelectric body in a same or opposite direction based on the concepts described above, not only is the laminated piezoelectric body able to increase sensitivity by three-fold (approximately 10 dB) or more when transmitting and receiving a 3λ/4 wave as compared to a case where residual polarizations or C axes or A axes of crystals of respective piezoelectric bodies are simply arranged in a same direction, the laminated piezoelectric body can also function as a filter that cancels a λ/4 wave. Furthermore, since the laminated piezoelectric body is electrically coupled in parallel, electrical impedance can be reduced to ⅓. As described above, a laminated piezoelectric body based on the concepts described above is extremely effective when selectively transmitting and receiving a 3λ/4 wave at a high S/N ratio. Accordingly, in the case of wave reception, a band separation filter or an amplifier may be eliminated. Alternatively, even when eliminating such components is not feasible, the order of such a filter can be lowered to suppress loss in a case where a laminated piezoelectric body based on the concepts described above functions as a filter, and a gain of such an amplifier can be reduced in a case where a laminated piezoelectric body based on the concepts described above functions as an amplifier.

Third Embodiment

The third embodiment relates to transmission and reception of third order harmonics by a transducer in which piezoelectric bodies with equal thickness are laminated in six layers. For the present embodiment, each piezoelectric body in the three-layer piezoelectric body shown in the second embodiment has been split into two piezoelectric bodies. In addition to further reducing electrical impedance by half in a case of parallel coupling, since an upper end electrode and a lower end electrode are connected to each other, an entire laminated piezoelectric body can be electrically shielded.

Figure 19A:
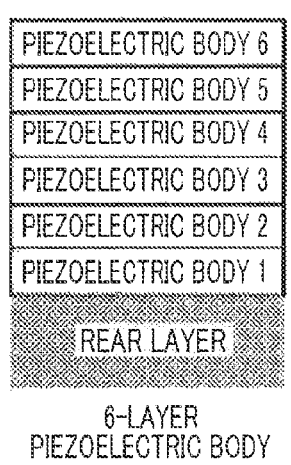
FIG. 19 is a sectional view schematically showing a structure of a six-layer piezoelectric transducer that is yet another detailed example of an embodiment conforming to the concept illustrated in FIG. 8.
Figure 19B:
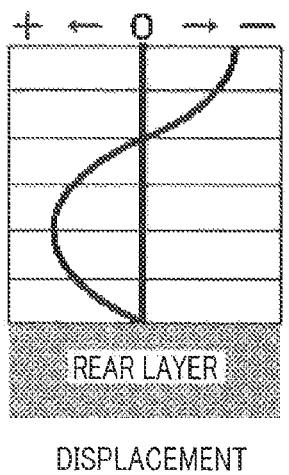
Figure 19C:
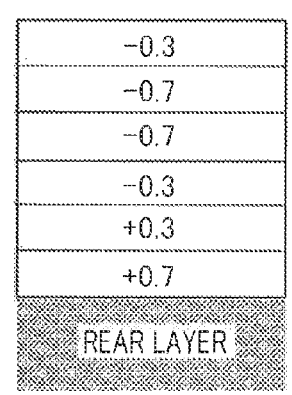

FIG. 19 is a sectional view which shows a structure of the six-layer piezoelectric body and which schematically shows displacement and distortion when transmitting and receiving third order harmonics. In a similar manner to FIG. 9, FIG. 19A represents a lamination condition. FIG. 19B shows displacements of the respective layers at a given moment, and FIG. 19C shows coefficients of distortions.

Distortions $S_1$, $S_2$, $S_3$, $S_4$, $S_5$, and $S_6$ of the respective piezoelectric bodies are given by Expression (46), Expression (47), Expression (48), Expression (49), Expression (50), and Expression (51) below Now, by adopting an approximation of $\frac{1}{2}^{1/2} \cong 0.7$, ratios of distortions of the respective piezoelectric bodies are as shown in the schematic view of FIG. 20.

$$S_1 = 6\xi_0 \sin(\pi/4)/h = 6\xi_0(1/2^{1/2}) \quad (46)$$

$$S_2 = 6\xi_0\{\sin(\pi/2) - \sin(\pi/4)\}/h = 6\xi_0(1 - 1/2^{1/2}) \quad (47)$$

$$S_3 = 6\xi_0\{\sin(3\pi/4) - \sin(\pi/2)\}/h = 6\xi_0(1/2^{1/2} - 1) \quad (48)$$

$$S_4 = 6\xi_0\{\sin(\pi) - \sin(3\pi/4)\}/h = 6\xi_0(-1/2^{1/2}) \quad (49)$$

$$S_5 = 6\xi_0\{\sin(5\pi/4) - \sin(\pi)\} = 6\xi_0(-1/2^{1/2}) \quad (50)$$

$$S_6 = 6\xi_0\{\sin(3\pi/2) - \sin(5\pi/4)\} = 6\xi_0(1/2^{1/2} - 1) \quad (51)$$

Figure 20:
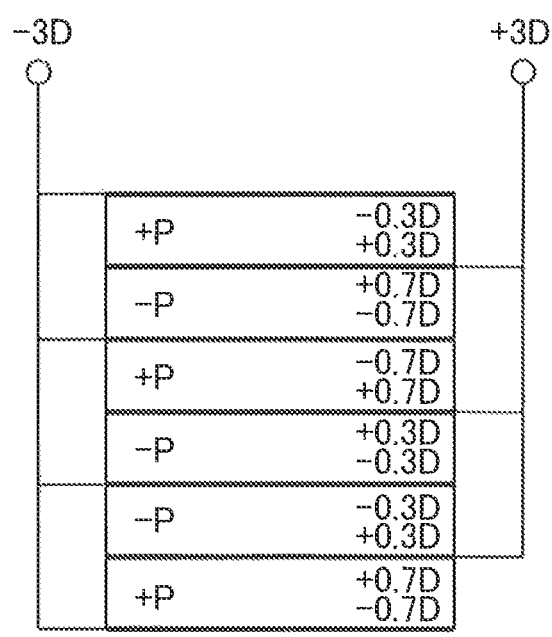
FIG. 20 is a diagram showing a relationship between an orientation of residual polarization of each piezoelectric body when detecting a third-order harmonic and electrical displacement due to a direct piezoelectric effect in the laminated piezoelectric body shown in FIG. 19.

FIG. 20 also shows a favorable arrangement of residual polarizations or C axes or A axes of crystals in a case were farther-side electrodes of mutually adjacent piezoelectric bodies are connected to each other to electrically couple the respective piezoelectric bodies in parallel. B adopting such a configuration, while net charge remains unchanged from the configuration of the three-layer lamination shown in FIG. 16, electrical impedance can be reduced to ½ of the configuration shown in FIG. 16.

FIG. 21 shows a result of a simulation of frequency characteristics of sensitivity in a six-layer piezoelectric: body that combines polarization arrangement and wiring as shown in FIG. 21. A right hand-side diagram in FIG. 21 shows a configuration thereof, while a left hand-side diagram in FIG. 21 shows characteristics thereof. A resonance frequency in a λ/4 resonance mode of the six-layer piezoelectric body is 5 MHz. However, by combining a polarization arrangement and wiring based on the concepts described above as shown in the right hand-side diagram, sensitivity in the λ/4 resonance mode attenuates and sensitivity in a ¾ resonance mode becomes maximum as shown in the left band-side diagram.

Moreover, the laminated piezoelectric body described above is not limited to an ultrasound transducer in an ultrasound diagnostic device and can also be applied to a fish finder or the like. In addition, transmission/reception signals of the laminated piezoelectric body described above are not limited to the ultrasound band, and the laminated piezoelectric body described above may also be applied to configurations in which a low-frequency stress is applied to generate power.

Fourth Embodiment

Figure 22:
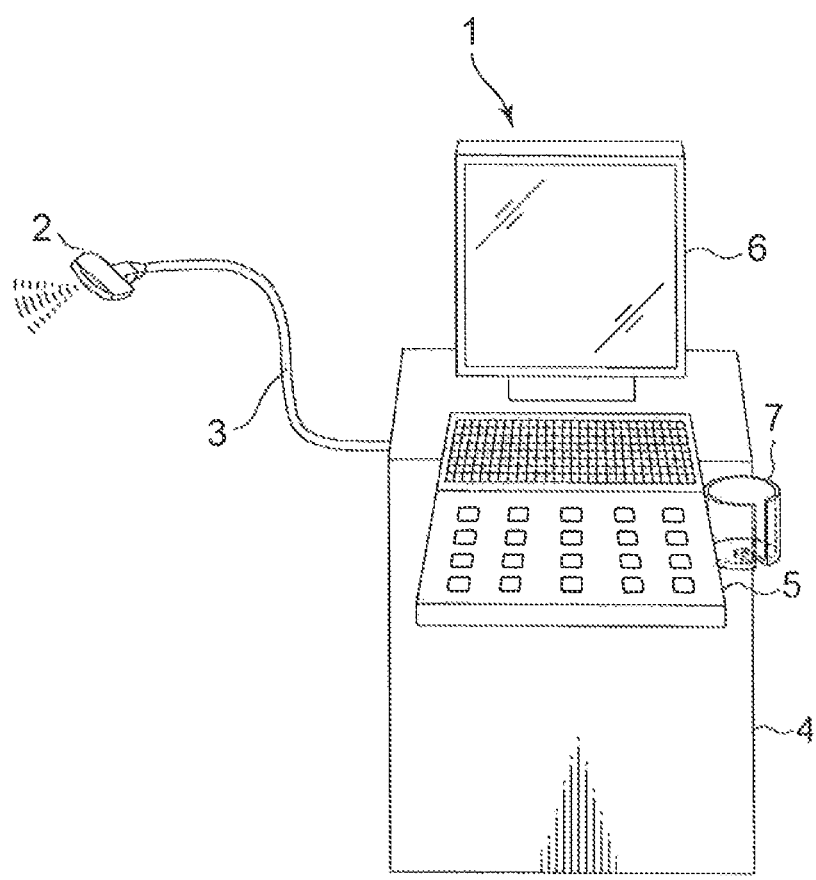
FIG. 22 is a perspective view showing an exterior structure of an ultrasound diagnostic device according to an embodiment.

While a laminated piezoelectric body based on the concepts described above can conceivably be applied to various products as described above, a case where such a laminated piezoelectric body is applied to an ultrasound diagnostic device will now be described. FIG. 22 is a perspective view showing an exterior structure of an Ultrasound diagnostic device according to an embodiment. The ultrasound diagnostic device 1 comprises: an ultrasound probe 2 which transmits an ultrasound wave toward a subject such as a living body (not shown) and which receives an ultrasound wave generated by reflection or the like by the living body; and a diagnostic device main body 4 which is connected to the ultrasound probe 2 via a cable 3, which causes the ultrasound probe 2 to transmit an ultrasound signal toward the subject by transmitting an electrical transmission signal via the cable 3, and which creates a tomographic image of an internal state of the subject based on a signal received by the ultrasound probe 2.

The diagnostic device main body 4 comprises an operating panel 5 and a display panel 6 in an upper portion thereof. The operating panel 5 is used to perform various setting operations and the like, while the display panel 6 displays images for supporting such operations, tomographic images created based on received ultrasound signals, and the like. In addition, a holder 7 that holds the ultrasound probe 2 when not in use is provided at an appropriate location on the operating panel 5 or the diagnostic device main body 4.

Figure 23:
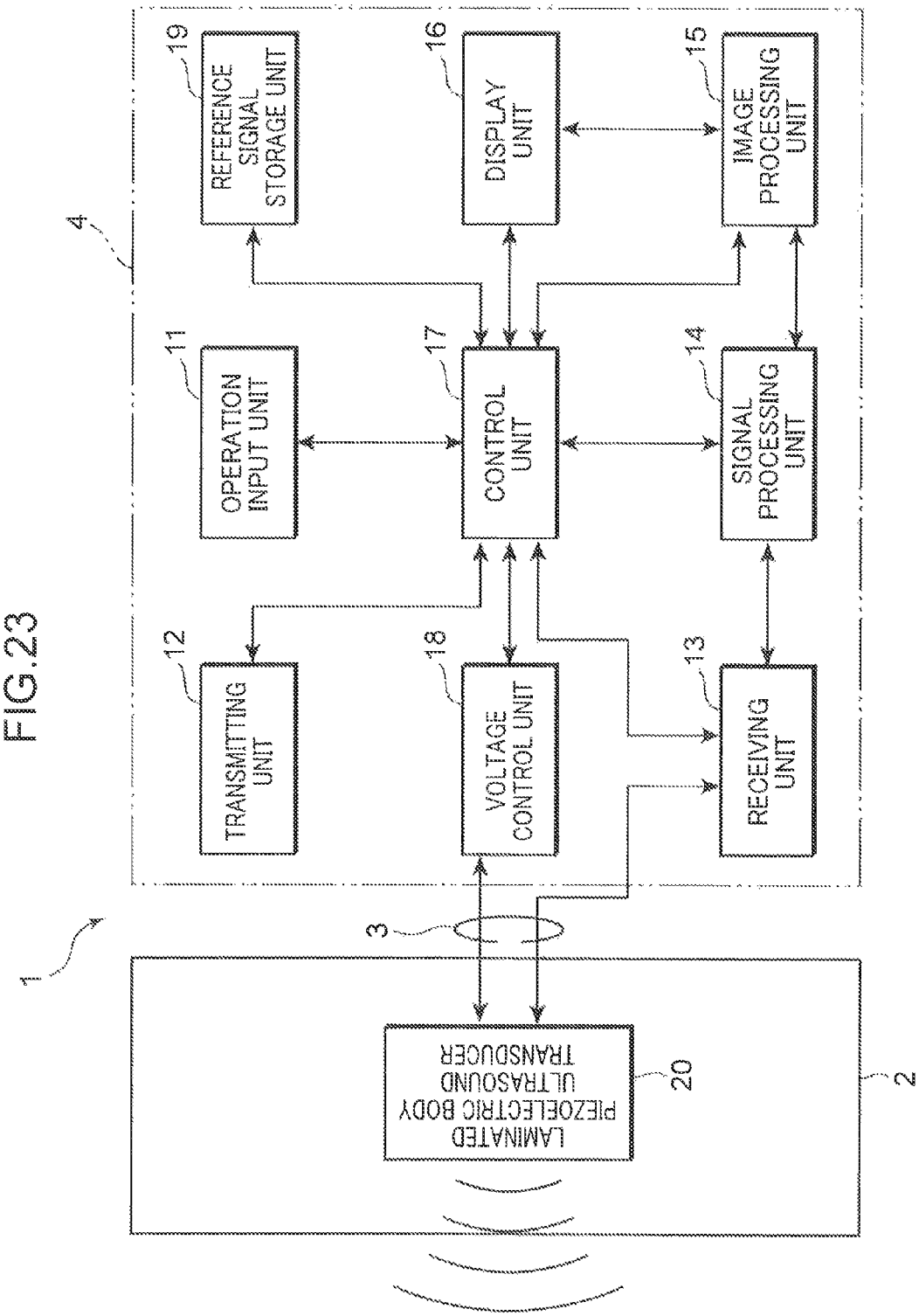
FIG. 23 is a block diagram slowing an electrical configuration of a diagnostic device main body of the Ultrasound diagnostic device shown in FIG. 22.

FIG. 23 is a block diagram showing an electric configuration of the diagnostic device main body 4. The diagnostic device main body 4 comprises an operation input unit 11 (of which the operating panel 5 is one example), a transmitting unit 12, a receiving unit 13, a signal processing unit 14, an image processing unit 15, a display unit 16 (of which the display panel 6 is one example), a control unit 17, a voltage control unit 18, and a reference signal storage unit 19.

The operation input unit 11 is constituted by an operating panel, a keyboard, or the like comprising a plurality of input switches, and is used to input a command for instructing the start of a diagnosis, data such as personal information of the subject, and the like.

The transmitting unit 12 is a circuit which generates a transmission pulse under control by the control unit 17 and which performs forming so that transmission pulses from respective piezoelectric elements of the ultrasound probe 2 focus at a predetermined focusing position. Furthermore, in the present embodiment, the transmission pulses described above are constituted by a plurality of coded pulses stretched in a temporal axis direction. A created transmission pulse is supplied to the voltage control unit 18 via the control unit 17, and after an amplitude thereof is expanded, the transmission pulse supplied to each piezoelectric element.

The receiving unit 13 is a circuit which receives an electric reception signal from the ultrasound probe 2 via the cable 3 by performing a predetermined reception process under control by the control unit 17, and outputs the reception signal to the signal processing unit 14.

The signal processing unit 14 performs correlation processing of an output of the receiving unit 13 and a reference signal set in advance in order to detect a received ultrasound wave from the output of the receiving unit 13. The reference signal is an approximation function derived from the order of third or higher order harmonics to be detected when a frequency of a transmitted ultrasound wave is a fundamental frequency, a diagnosed region of the subject, and diagnostic depth.

Moreover, prior to performing the correlation processing, the signal processing unit 14 compresses the coded pulse in the temporal axis direction to create a reception pulse that corresponds to the transmission pulse. By using such coded pulses, an impact of a transmission pulse on a living body that is the subject can be prevented from becoming significant and a reception pulse with a large amplitude or, in other words, a favorable S/N is obtained. By combining a decoding filter that extracts only such third or higher order harmonics with a bandpass filter, changing the type of coded pulses, or the like, both S/N improvement and extraction of the third or higher order high-frequency waves can be achieved, Known and conventional means may be used to perform stretching and compression processes using the coded pulses, and a processing technique therefor is described in, for example, Japanese Patent Application Publication No. 2003-225217.

The reference signal storage unit 19 is configured so as to comprise a storage element such as a ROM (Read Only Memory) or an EEPROM (Electrically Erasable Programmable Read Only Memory), and stores approximation functions corresponding to a plurality of diagnosis domains and diagnostic depths in the subject as the reference signals. The signal processing unit 14 performs correlation processing by selecting a single reference signal from the plurality of reference signals (approximation functions) stored in the reference signal storage unit 19 in correspondence with the diagnosis domains and the diagnostic depths of the subject. In addition, the transmitting unit 12 performs beam forming in response to the selected reference signal. The diagnosis domains and the diagnostic depths are inputted using the operation input unit 11.

The image processing unit 15 is a circuit which, under control of the control unit 17, generates an image (ultrasound image) of an internal state of the subject based on a reception signal subjected to correlation processing by the signal processing unit 14.

The display unit 16 is a device which, under control of the control unit 17, displays the ultrasound image of the subject generated by the image processing unit 15. The display unit 16 is a display device such as a CRT display, an LCD, an organic display, and a plasma display, a printing device such as a printer, or the like.

The control unit 17 is a circuit which comprises a microprocessor, a storage element, peripheral circuits thereof, and the like and Which controls the entire ultrasound diagnostic device 1 by respectively controlling the operation input unit 11, the transmitting unit 12, the voltage control unit 18, the receiving unit 13, the signal processing unit 14, the reference signal storage unit 19, the image processing unit 15, and the display unit 16 according to their functions.

Figure 24:
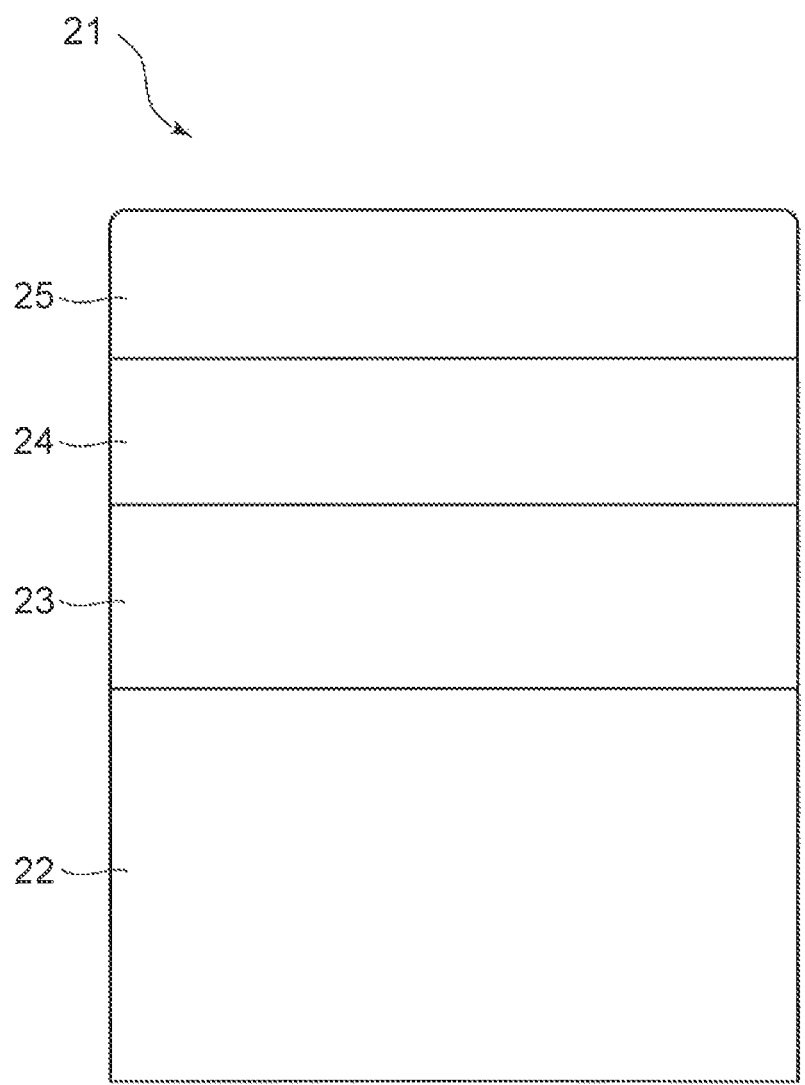
FIG. 24 is a sectional view schematically showing an example of a structure of an ultrasound transducer of an ultrasound probe in the Ultrasound diagnostic device shown in FIG. 22.

FIG. 24 is a sectional view schematically showing a structure of an ultrasound transducer 21 which is used as an ultrasound transducer 20 in the ultrasound probe 2 described above. The ultrasound transducer 21 comprises a plurality of piezoelectric elements arranged in a same straight line, and an arrangement direction of the piezoelectric elements is a direction perpendicular to the paper plane in FIG. 24 (a thickness direction). The ultrasound transducer 21 is basically an organic-inorganic; laminated ultrasound transducer configured such that a transmitting piezoelectric layer 23, an intermediate layer 24, and a receiving piezoelectric layer 25 are sequentially laminated in this order on a backing layer (rear layer) 22. The transmitting piezoelectric layer 23 is formed of an inorganic material so as to enable large power transmission and is laminated on top of the backing layer 22. The receiving piezoelectric layer 25 is provided on a subject side of the transmitting piezoelectric layer 23 via the intermediate layer 24 and is formed of an organic material capable of receiving a harmonic band for harmonic imaging. A transmission pulse from the voltage control unit 18 is supplied to the transmitting piezoelectric layer 23 that is a second piezoelectric body, while a reception signal received by the receiving piezoelectric layer 25 that is a first piezoelectric body is supplied to the receiving unit 13.

The intermediate layer 24 is provided between the transmitting piezoelectric layer 23 and the receiving piezoelectric layer 25 in order to alleviate a difference in acoustic impedances between the transmitting piezoelectric layer 23 and the receiving piezoelectric layer 25, In the present embodiment, an acoustic impedance of the receiving piezoelectric layer 25 approaches an acoustic impedance of a living body that is a subject due to the receiving piezoelectric layer 25 being formed of an organic material such as those described later and, as a result, an acoustic matching layer is not provided on the subject side of the receiving piezoelectric layer 25, In this manner, the ultrasound transducer 21 has a simplified structure. Moreover, an acoustic lens may be provided on the receiving piezoelectric layer 25 as necessary.

In the ultrasound transducer 21 configured as described above, any one of the laminated piezoelectric bodies described earlier with reference to FIGS. 8, 9, 12, 16, and 20 is used in the receiving piezoelectric layer 25 formed of an organic material. In addition, when a transmitted ultrasound wave has a wavelength of $\lambda$, the transmitting piezoelectric layer 23 resonates in a $\lambda/4$ resonance mode, the receiving piezoelectric layer 25 resonates in a $3\lambda/4$ resonance mode, and the receiving piezoelectric layer 25 extracts third order harmonics with a wavelength of $\lambda$ at a high gain as described earlier to remove a fundamental wave. Accordingly, the ultrasound diagnostic device 1 according to the present embodiment is able to eliminate the need for a filter and an amplifier in the receiving unit 13 or, alternatively, even when such a filter and an amplifier is used, the ultrasound diagnostic device 1 is capable of reducing the order of the filter and reducing the gain of the amplifier. Furthermore, since the ultrasound transducer 21 according to the present embodiment is capable of using an inorganic piezoelectric body and an organic piezoelectric body respectively suitable for transmission and reception, the ultrasound probe 2 is realized which is well suited for harmonic imaging in which large power transmission is performed and harmonics generated by a subject are received at high gain.

Figure 25:
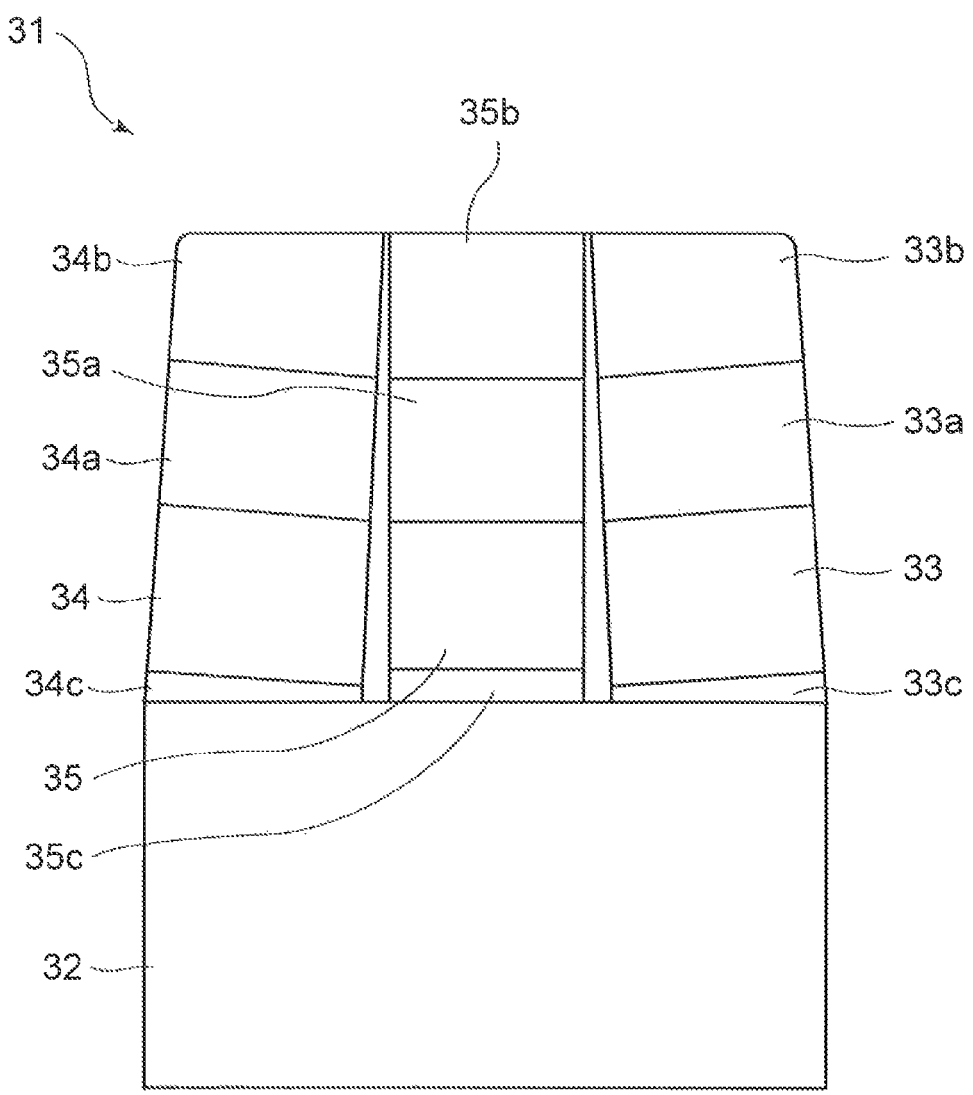
FIG. 25 is a sectional view schematically showing another example of a structure of an ultrasound transducer of an ultrasound probe in the ultrasound diagnostic device shown in FIG. 22.

Meanwhile, FIG. 25 is a sectional view schematically showing a structure of another ultrasound transducer 31 which is used as the ultrasound transducer 20 in the ultrasound probe 2 described above. The ultrasound transducer 31 also comprises a plurality of piezoelectric elements arranged in a same straight line, and an arrangement direction of the piezoelectric elements is a direction perpendicular to the paper plane in FIG. 25 (a thickness direction). The ultrasound transducer 31 is an organic-inorganic parallel ultrasound transducer in which an organic piezoelectric body and an inorganic piezoelectric body are arranged in parallel. In the ultrasound transducer 31, a receiving piezoelectric layer 35 formed of an organic material capable of receiving a harmonic band for harmonic imaging is provided at center in a width direction on a hacking layer (rear layer) 32 in the same straight line, and transmitting piezoelectric layers 33 and 34 formed of an inorganic material capable of large power transmission are provided in parallel on both sides of the receiving piezoelectric layer 35 in a width direction thereof.

In addition, acoustic matching layers 33a, 34a, and 35a for matching acoustic impedance with a living body that is a subject and acoustic lenses 33h, 34h, and 35b for focusing ultrasound waves are respectively laminated on the piezoelectric layers 33, 34, and 35. Furthermore, interposed members 33c, 34c, and 35c are respectively interposed between the piezoelectric layers 33, 34, and 35 and the backing layer 32. The interposed member 35c of the central receiving piezoelectric layer 35 is a flat plate, while the interposed members 33c and 34c of the transmitting piezoelectric layers 33 and 34 on both sides are formed in a wedge shape in order to cause the transmitting piezoelectric layers 33 and 34 to tilt inward to the side of the receiving piezoelectric layer 35. In other words, the interposed members 33c and 34c are formed so that thicknesses thereof gradually increase from center outward. Note that, in FIG. 25, the inward tilt angles of the wedge-shaped interposed members 33c and 34c are drawn larger than in reality for better understanding.

In the ultrasound transducer 31 configured as described above, any one of the laminated piezoelectric bodies described earlier with reference to FIGS. 3, 9, 12, 16, and 20 is used in the receiving piezoelectric layer 35 formed of an organic material. In addition, when a transmitted ultrasound wave has a wavelength of $\lambda$, the transmitting piezoelectric layers 33 and 34 resonate in a $\lambda/4$ resonance mode, the receiving piezoelectric layer 35 resonates in a $3\lambda/4$ resonance mode, and the receiving piezoelectric layer 35 extracts third order harmonics with a wavelength of $\lambda$ at a high gain as described earlier to remove a fundamental wave. Accordingly, the ultrasound diagnostic device 1 according to the present embodiment is able to eliminate the need for a filter and an amplifier in the receiving unit 13 or, alternatively, even when such a filter and an amplifier is used, the ultrasound diagnostic device 1 is capable of reducing the order of the filter and reducing the gain of the amplifier. Furthermore, since the ultrasound transducer 31 according to the present embodiment is capable of using an inorganic piezoelectric body and an organic piezoelectric body respectively suitable for transmission and reception, the ultrasound probe 2 is realized which is well suited for harmonic imaging in which large power transmission is performed and harmonics generated by a subject are received at high gain.

Hereinafter, a specific preparation method and materials of a laminated piezoelectric body that is used as the receiving piezoelectric layers 25 and 35 which perform resonance in the $3\lambda/4$ resonance mode will be described in detail. Generally, an ultrasound vibrator is constructed by arranging a pair of electrodes on both sides of a piezoelectric layer (also referred to as a piezoelectric body layer, a piezoelectric film, and a piezoelectric body film) formed of a film-like piezoelectric material. In addition, the ultrasound transducer 20 is constructed by arranging a plurality of vibrators (piezoelectric elements) one-dimensionally or two-dimensionally. In order to arrange the plurality of vibrators, a method is used in which a single vibrator is bonded to a backing layer, and after an acoustic matching layer or the like is bonded as necessary, dicing is performed to split the vibrator into respective elements.

An aspect ratio Win of each element of the laminated vibrator split in plurality favorably ranges from 0.4 to 0.6, where W denotes an azimuth direction width and H denotes height. This is because interference between a vibration in a transmitting/receiving direction in which ultrasound waves propagate and a vibration (lateral vibration) in a scanning direction (arrangement direction) that is perpendicular to the transmitting/receiving direction can be suppressed, narrowing of directional characteristics of the vibrator in the arrangement direction can be avoided, and favorable sensitivity can be maintained even with a large angle of deflection without limiting an angle of beam spread.

In addition, the laminated piezoelectric body has a function of setting a predetermined number of vibrators in a long axis direction in which the plurality of vibrators are arranged as a bore, drives a plurality of vibrators belonging to the bore so as to focus and irradiate an ultrasound beam on a measurement region inside a subject and, at the same time, receiving an ultrasound reflection echo or the like emitted by the subject using a plurality of vibrators belonging to the bore or a plurality of vibrators that differ from those belonging to the bore and converting the ultrasound reflection echo into an electrical signal.

In a case where a laminated piezoelectric body is formed of an inorganic material such as ceramics in order to realize the laminated piezoelectric bodies shown in FIGS. 8, 9, 12, 16, and 20, a piezoelectric body layer and an electrode layer are laminated and then integrated by firing or the like.

On the other hand, in a case where a laminated piezoelectric body is formed of an organic material such as PVDF, the laminated piezoelectric body is integrally formed by forming an electrode layer on a part of or all of front and back surfaces, laminating an organic material sheet subjected to a polarization treatment, and connecting interlayers with an adhesive, in this case, contact surfaces of the electrode layer favorably overlap each other. This is to prevent an unnecessary electric field and a non-uniform sound field from forming during driving of the vibrator or reception of an ultrasound wave. Although the adhesive has an insulating property, rough surfaces (minute irregularities) of an organic material layer and an electrode layer penetrate each other upon lamination and, as a result, adjacent electrodes enter a conduction state. After lamination and adhesion, unnecessary portions at the ends of the vibrator are cut off and the vibrator is molded into a size mountable on a transducer. Subsequently, in order to connect the respective piezoelectric bodies in parallel, electrode extraction directions are switched for every other piezoelectric body, and the respective electrodes are connected by a conductive paste. As a result, a signal electrode and a GNU electrode are respectively extracted on both side portions on the side of the backing layers 22 and 32.

Examples of materials for the laminated piezoelectric body include inorganic piezoelectric materials such as conventionally used quartz, piezoelectric ceramics including PZT and PZLT, and a thin film of piezoelectric single crystals such as PZN-PT, PMN-PT, $LiNbO_3$, $TaO_3$, $KNbO_3$, ZnO, and AlN, as well as organic piezoelectric materials such as polyvinylidene fluoride and polyvinylidene fluoride-type copolymers, polyvinylidene cyanide and vinylidene cyanide-type copolymers, odd nylons such as nylon 9 and nylon 11, aromatic nylon, alicyclic nylon, polylactic acid, polyhydroxy carboxylic acids such as polyhydroxybutylate, cellulosic derivatives, and polyurea. In addition, composite materials using a combination of an inorganic piezoelectric material and an organic piezoelectric material or a combination of an inorganic piezoelectric material and an organic polymeric material may also be used. In the ultrasound transducers 21 and 31 shown in FIGS. 24 and 25, the inorganic material described above is used for the transmitting piezoelectric layers 23; 33, and 34, and the organic material described above is used for the receiving piezoelectric layers 25 and 35.

A thickness of a single layer in the laminated piezoelectric body is dependent on a set center frequency (wavelength $\lambda$) and favorably ranges within 5 to 200 μm, in consideration of workability. Since adopting a same thickness for the respective piezoelectric bodies 1 to 3 or the like enables the respective piezoelectric bodies to be manufactured with greater ease, productivity may be improved with the ultrasound transducers 21 and 31 configured as described above.

Favorable methods of forming a piezoelectric layer formed of an organic piezoelectric material include a method of forming a film by coating and a method of forming a film by vapor deposition (vapor deposition polymerization). Examples of coating methods include spin coating, solvent casting, melt casting, melt pressing, roll coating, flow coating, printing, dip coating, and bar coating, in addition, as a vapor deposition (vapor deposition polymerization) method, a film can be obtained by evaporating a monomer from a single evaporation source or a plurality of evaporation sources in a vacuum of around several hundred Pa or lower, and depositing and reacting the monomer on a substrate. Temperature adjustment of the substrate is appropriately performed when necessary.

When forming an electrode layer on the organic piezoelectric body film created as described above, first, an underlaying metal such as titanium (Ti) or chrome (Cr) is formed by sputtering to a thickness of 0.02 to 1.0 μm. Then, a metallic material mainly consisting of a metallic element or a metallic material formed by an alloy of the metallic element, to which an insulating material is partially added if necessary, is formed by an appropriate method such as sputtering to a thickness of 1 to 10 μm. Subsequently, a polarization treatment of the piezoelectric layer (piezoelectric body film) is performed. Gold (Au), platinum (Pt), silver (Ag), palladium (Pd), copper (Cu), nickel (Ni), tin (Sn), or the like is used as the metallic material. Besides the sputtering described above, electrode formation can also be performed by applying a conductive paste which combines a fine metal powder with low-melting-point glass by screen printing, dipping, spraying, or the like.

Meanwhile, a formation method of the acoustic matching layers 33a, 34a, and 35a and the acoustic lenses 33b, 34b, and 35b which are formed in the ultrasound transducer 31 shown in FIG. 25 is as follows. In order to prevent an occurrence of a reflection at an interfacial boundary due to a difference in acoustic impedance between a vibrator and body tissue and to prevent prolonged free vibration, the acoustic matching layers 33a, 34a, and 35a are interposed between the vibrator and the body tissue and have an acoustic impedance that is intermediate between the two. By interposing the acoustic matching layers, the reflection at the interfacial boundary is reduced and free vibration converges rapidly, pulse widths of ultrasound pulses transmitted and received by the transducer become shorter, and ultrasound waves are effectively propagated into the living body.

Examples of materials used for the acoustic matching layers 33a, 34a, and 35a include metallic materials (such as aluminum, aluminum alloys (for example, Al—Mg alloy), and magnesium alloys), glass (such as MACOR glass, silicate glass, and fused silica), carbon materials (such as carbon graphite and copper graphite), and resin materials (such as polyethylene (PE), polypropylene (PP), polycarbonate (PC), nylon (PA6, PA6-6), polyphenylene sulfide (PPS, glass fiber-polyphenylene allowed), polyphenylene ether (PPE), polyether ether ketone (PEEK), polyamide-imide (PAI), polyethylene terephthalate (PETP), epoxy resins, urethane resins, ABC resins, ABS resins, AAS resins, and AES resins). A thermosetting resin such as epoxy resin to which zinc oxide, titanium oxide, silica, alumina, red iron oxide, ferrite, tungsten oxide, ytterbium oxide, barium sulfate, tungsten, molybdenum, or the like is added as a filler and which is then molded is favorably used as the material of the acoustic matching layers 33a, 34a, and 35a.

The acoustic matching layers 33a, 34a, and 35a may be single layers or may be constituted by a plurality of layers. Favorably, the acoustic matching layers 33a, 34a, and 35a consist of two or more layers. A thickness of the acoustic matching layers 33a, 34a, and 35a must be determined so as to be $\lambda/4$ when a transmitted ultrasound wave has a wavelength of $\lambda$ (in FIGS. 24 and 25, the thickness is greater because a velocity of an ultrasound wave is greater in the transmitting piezoelectric layers 23; 33, and 34 than in the receiving piezoelectric layers 25 and 35). In the case where the above requirement is not satisfied, this causes a plurality of spurious portions to appear in a frequency that differs from an original resonance frequency, which in turn causes a significant fluctuation in fundamental acoustic characteristics and a decline in sensitivity and S/N due to an increase in reverberation time and a waveform distortion of a reflection echo. The thickness of such acoustic matching layers 33a, 34a, and 35a is approximately within a range of 30 μm to 500 μm.

In addition, the backing layers 22 and 32 are arranged on a back surface of the ultrasound vibrator and suppress (absorb) propagation of ultrasound waves emitted backward. Accordingly, unnecessary reflection toward the side of the vibrator is suppressed and pulse width can be shortened. Examples of materials used for the backing layers 22 and 32 include materials created by adding a powder such as tungsten oxide, titanium oxide, and ferrite to natural rubber, ferrite rubber, or epoxy resin and then performing press molding, thermoplastic resins such as vinyl chloride, polyvinyl butyral (PVB), ABS resin, polyurethane (PUR), polyvinyl alcohol (PVAL), polyethylene (PE), polypropylene (PP), polyacetal (POM), polyethylene terephthalate (PETP), fluororesin (PTFE), polyethylene glycol, and polyethylene terephthalate-polyethylene glycol copolymer, and the like.

Backing materials are favorably made of a rubber composite and/or an epoxy resin composite, and a shape thereof can be selected as appropriate according to a shape of the piezoelectric body or a shape of a probe head including the piezoelectric body.

The rubber composite favorably contains a rubber component and a filler and has a hardness ranging from A70 according to a type A durometer to D70 according to a type D durometer among spring-type hardness testers (durometer hardness) conforming to JIS K6253, and various other compounding agents may be further added as necessary.

Favorable examples of the rubber component include ethylene-propylene rubber (EPDM or EPM), hydrogenated nitrile rubber (HNBR), chloroprene rubber (CR), silicone rubber, a blend rubber of EPDM and HNBR, a blend rubber of EPDM and nitrile rubber (NBR), a blend rubber of NBR and/or HNBR and high styrene rubber (HSR), and a blend rubber of EPDM and HSR. More favorable examples include ethylene-propylene rubber (EPDM or hydrogenated nitrile rubber (HNBR), a blend rubber of EPDM and HNBR, a blend rubber of EPDM and nitrile rubber (NBR), a blend rubber of NBR and/or HNBR and high styrene rubber (HSR), and a blend rubber of EPDM and HSR. While a single rubber component such as vulcanized rubber and a thermoplastic elastomer may be used independently as the rubber component according to the present embodiment, a blend rubber that is a blend of two or more rubber components may also be used.

As the filler that is added to the rubber component, a wide range of fillers from those ordinarily used to those with high specific gravity may be selected in various compounding quantities and shapes. Examples of fillers include metallic oxides such as zinc oxide, titanium white, red iron oxide, ferrite, alumina, tungsten trioxide, and ytterbium oxide, days such as calcium carbonate, hard clay, and diatomite, metallic salts such as calcium carbonate and barium sulfate, glass powders, fine metallic powers of tungsten, molybdenum, and the like, and various balloons such as glass balloons and polymer balloons. Although the fibers may be added at various ratios, the fibers are favorably added at around 50 to 3000 parts by mass with respect to 100 parts by mass of the rubber component, and more favorably added at around 100 to 2000 parts by mass or around 300 to 1500 parts by mass. In addition, the fillers may be added singularly or as a combination of two or more fillers.

Other compounding agents such as a vulcanizing agent, a cross-linking agent, a hardening agent, auxiliary agents thereof, a degradation preventing agent, an antioxidant, and a coloring agent may be added to a rubber composite as necessary. For example, carbon black, silicon dioxide, processing oil, sulphur (a vulcanizing agent), dicurnyl peroxide (Dicup, a cross-linking agent), and stearic acid may be compounded. While these compounding agents are used as necessary, generally, the compounding agents are respectively used in quantities of around 1 to 100 parts by mass with respect to 100 parts by mass of the rubber component, and such quantities are varied as appropriate according to overall balance and characteristics.

The epoxy resin composite favorably contains an epoxy resin component and a filler, and various compounding agents are further added as necessary. Examples of the epoxy resin component include bisphenol A, bisphenol F, resol novolac, phenol modified novolac, and other novolac-type epoxy resins, naphthalene structure-containing polycyclic aromatic epoxy resin, anthracene structure-containing polycyclic aromatic epoxy resin, fluorene structure-containing polycyclic aromatic epoxy resin and other polycyclic aromatic epoxy resins, hydrogenerated alicyclic epoxy resins, and liquid-crystalline epoxy resins. While the epoxy resin component according to the present embodiment may be used independently, two or more epoxy resin components may be used mixed in a similar manner to blended resins.

As the filler added to the epoxy resin component, various fillers from those similar to the aforementioned fillers that are added to the rubber component to composite particles created by pulverizing the rubber composite may be favorably used. Examples of the composite particles include those obtained by pulverizing silicone rubber filled with ferrite with a pulverizer to a particle size of around 200 μm.

When using the epoxy resin compound, a cross-linking agent must be further added, examples of which include diethylene trianiine, triethylenetetramine, dipropylene diamine, diethylamino propylamine and other chain aliphatic polyamines, N-aminoethylpiperazine, menthene diamine, isophorone diamine and other cyclic aliphatic polyamines, m-xylene diamine, meta-phenylenediamine, diaminodiphenyl methane, diaminodiphenyl sulfone and other aromatic amines, polyamide resin, piperidine, NN-dimethylpiperazine, triethylenediaminc, 2,4,6-tris(dimethylaminomethyp-phenoi, benzyldimethylamine, 2-(dimethylaminomethyl) phenol and other secondary and tertiary amines, 2-methylimidazole, 2-ethylimidazole, 1-cyanoethyl-2-undecyl imidazolium trimellitate and other imidazoles, liquid polymercaptan, polysulfide, phthalic anhydride, trimellitic anhydride, methyltetrahydrophthalic acid anhydride, methyl endo methylene tetrahydrophthalic anhydrite, methyl butenyl tetrahydrophthalic anhydrite, methyl hexahydrophthalic acid and other acid anhydrides.

The backing layers 22 and 32 formed as described above favorably have a thickness of around 1 to 10 mm and more favorably 1 to 5 mm.

Meanwhile, the acoustic lenses 33b, 34b, and 35b are provided in order to converge ultrasound waves using refraction and to improve resolution. Requirements for the acoustic lenses 33b, 34b, and 35b include being able to converge ultrasound waves, being capable of coming into close contact with the living body that is a subject to match acoustic impedances (density×sound velocity: (1.4 to 1.6)×106 kg/m$^2$·sec) between the side of the piezoelectric layers 33, 34, and 35 and the living body in order to reduce reflection of ultrasound waves, and the lenses themselves having low ultrasound attenuation. Therefore, acoustic lenses created based on a polymeric material have conventionally been provided.

With a desirable lens material, sound velocity thereof is sufficiently lower than that of the human body, attenuation thereof is low, and an acoustic impedance thereof is similar to a value of human skin if the sound velocity of the lens material is sufficiently lower than that of a human body, the lens may be given a convex shape which improves sliding during a diagnosis and thereby enabling the diagnosis to be performed safely. In addition, low attenuation enables ultrasound waves to be transmitted and received with good sensitivity. Furthermore, if the acoustic impedance is similar to a value of human skin, since reflection decreases or, in other words, transmissivity increases, ultrasound waves can be similarly transmitted and received with better sensitivity.

In the present embodiment, as materials that constitute the acoustic lenses 33b, 34b, and 35b, conventional and known silicone-based rubbers, butadiene-based rubbers, polyurethane rubber, epichlorohydrin rubber and other homopolymers, and copolymer rubbers such as ethylene-propylene copolymer rubber formed by copolymerizing ethylene and propylene can be used Among the above, silicone-based rubbers are particularly favorably used.

Examples of silicon-based rubbers usable in the present embodiment include silicone rubber and fluorine silicone rubber. In particular, silicone rubber is favorably used in consideration of lens material characteristics. Silicone rubber refers to organopolysiloxane having a molecular frame made of Si—O bonds and a plurality of organic groups primarily attached to the Si atoms. Normally, a main component of the organopolysiloxane is methyl polysiloxane and 90% or more of all organic groups are methyl groups. Hydrogen atoms, phenyl groups, vinyl groups, allyl groups, and the like may be introduced instead of the methyl groups. For example, the silicone rubber can be obtained by mixing a hardening agent (a vulcanizing agent) such as benzoyl peroxide into highly polymerized organopolysiloxane, and hardening the mixture by heating and vulcanizing. An organic or inorganic filler such as silica and nylon powder, a vulcanizing assistant such as sulfur and zinc oxide and the like may be added as necessary.

Examples of butadiene based rubber used in the present embodiment include copolymer rubber solely consisting or mainly consisting of butadiene and having a small amount of styrol or acrylonitrile copolymerized with the butadiene. In particular, butadiene rubber is favorably used in consideration of lens material characteristics, Butadiene rubber refers to a synthetic rubber obtained by a polymerization of butadiene having conjugated double bonds. Butadiene rubber can be obtained by an 1.4 to 1.2 polymerization of butadiene having conjugated double bonds as a single constituent, Butadiene rubber is favorably vulcanized using sulfur and the like.

The acoustic lenses 33b, 34b, and 35b according to the present embodiment may be obtained by mixing a silicone-based rubber and a butadiene-based rubber and then vulcanizing and hardening the mixture. More specifically, this can be achieved by mixing silicone rubber and butadiene rubber at an appropriate ratio using a mill roll, adding a vulcanizing agent such as benzoyl peroxide, performing heating and vulcanization, and finally performing cross-linking (hardening). In doing so, zinc oxide is favorably added as a vulcanizing assistant. Zinc oxide is capable of promoting vulcanization and reducing vulcanization time without compromising lens characteristics. Furthermore, a coloring agent and other additives may be added in an amount which does not compromise Characteristics of the acoustic lenses. Normally, in order to obtain an acoustic impedance approximating that of a human body, a sound velocity lower than that of a human body, and low attenuation, the silicone-based rubber and the butadiene-based rubber are favorably mixed at a ratio of 1:1. However, the mixture ratio can be modified as appropriate.

Silicone rubbers are commercially available, and usable examples thereof include KE742U, KE752U, KE931U, KE941U, KE951U, KE961U, KE850U, KE555U, and KE575U manufactured by Shin-Etsu Chemical Co., Ltd., TSE221-3U, TE221-4U, TSE2233U, XE20-523-4U, TSE27-4U, TSE260-3U, and TSE-260-4U manufactured by Momentive Performance Materials Inc., and SH35U, SH55UA, SH831U, SE6749U, and SE1120U, SE4704U manufactured by Dow Corning Toray Co., Ltd.

Moreover, in the present embodiment, for the acoustic lenses 33b, 34b, and 35b, an inorganic filler such as silica, alumina, and titanium oxide or an organic resin such as nylon can be mixed depending on intended use such as sound velocity adjustment and density adjustment to a rubber material base (main component) such as silicone-based rubber described above. In addition, a substance which emits light when irradiated by an excitation light or, in other words, a luminescent material may be added to a region of the acoustic lenses 33b, 34b, and 35b in proximity to a surface of the subject.

A generally used epoxy-based resin is suitable for adhesion between members used in the present embodiment. Specific examples of commercially available epoxy adhesives include DP-420, DP-460, and DP-460EG manufactured by Sumitomo 3M Limited, Excel-EPO, EP001, EP008, EP330, and EP331 manufactured by Cemedine Co., Ltd., Araldite Standard (registered trademark) and Araldite Rapid (registered trademark) manufactured by Huntsman Advanced Materials, System Three Epoxy and GelMagic manufactured by System Three Resins, Inc., 2087L (high-strength two-component epoxy-containing resin), 2082C (room temperature-curable two-component epoxy resin with high-shear bond strength), and 2081D (soft polyvinyl chloride epoxy-based adhesive) manufactured by ThreeBond. Co., Ltd., E Set L manufactured by Konishi Co., Ltd., and 4525IP, 7050, NM25, and 44611P manufactured by Cotronies Corp. However, strong adhesion, low reactivity, and the like are required in consideration of dicing suitability, chemical resistance, and the like. Furthermore, since an adhesion layer is desirably made thin as possible, a low viscosity adhesive is favorable. Favorably, to adhesion layer has a thickness of 0.5 to 3 μm.

A method of fabricating a piezoelectric body will be described below. First, an inorganic piezoelectric body that is used as the transmitting piezoelectric bodies 23; 33, and 34 will be described. $CaCO_3$, $La_2O_3$, $Bi_2O_3$, and $TiO_2$ as constituent materials and MnO as an accessory constituent material were prepared and weighed so that the constituent materials had a final composition of $(Ca_{0.97}La_{0.03})Bi_{4.01}Ti_4O_{15}$.

Next, pure water was added thereto, and the pure water mixture was mixed for 8 hours by a ball mill with zirconia media and then sufficiently dried to obtain a mixed powder. The obtained mixed power was provisionally molded and then calcinated in air for 2 hours at 800° C. to fabricate a calcinated article.

Next, pure water was added to the obtained calcinated article, and the calcinated article was pulverized in pure water by a ball mill with zirconia media and then dried to fabricate a piezoceramic material powder. For the pulverization, piezoceramic material powders with particle sizes of 100 nm were respectively obtained by varying pulverization durations and conditions.

6 percent by mass of pure water was added as a binder to the respective piezoceramic material powders with different particle sizes. The powders were subjected to press molding to obtain a plate-like temporary compact with a thickness of 100 μm, and the plate-like temporary compact was vacuum-packed and then molded by pressing under a pressure of 235 MPa.

Next, the compact was fired, and a final sintered compact had a thickness of 20 μm. The firing was performed respectively at a temperature of 1100° C. Subsequently, an electric field of 1.5×Ec (MV/M) or higher was applied for 1 minute to perform a polarization treatment.

Next, a method of fabricating an organic piezoelectric body that is used as the receiving piezoelectric bodies 25 and 35 will be described. An organic piezoelectric material according to the present embodiment contains the polymeric material described earlier as a main component and has a film-like form that is stretchable at a temperature equal to or higher than room temperature and lower than melting point by 10° C. or more, and can be fabricated by performing a heat treatment while maintaining tension within a constant range and then performing second-stage stretching while being cooled down to room temperature.

When using an organic piezoelectric material such as vinylidene fluoride according to the present embodiment as a vibrator, the organic piezoelectric material is formed into a film and a surface electrode used to input electrical signals is then formed. Although it is a feature of the present embodiment that an electric field is applied in a thickness direction via an electrode formed on a surface and polarization is performed while applying compression, a similar effect may be achieved without forming an electrode on a surface by installing an electrode to which voltage is applied to a surface in contact with a material constituting a compressed member and then similarly applying an electric field in a thickness direction of the material while applying compression to perform polarization.

Film formation can be performed using a general method such as melting and casting. In a case of a polyvinylidene fluoride-trifluoroethylene copolymer which is known to have a crystal form that is spontaneously polarized simply by being formed into a film, it is useful to apply a treatment for adjusting molecular arrangement in order to further enhance characteristics. Examples of means thererfor include stretching and polarization treatment.

Various known methods may be adopted to perform stretching. For example, a method of stretching may involve casting a solution of the polymeric material described earlier melted in an organic solvent such as ethyl methyl ketone (MEK) onto a substrate such as a glass plate, drying the solvent at room temperature to obtain a film with a desired thickness, and stretching the film at room temperature at a predetermined stretching ratio to a given length. The stretching may be performed either uniaxially or biaxially as long as the organic piezoelectric material given a predetermined shape is not destroyed. The stretching ratio ranges from 2 to 10 and favorably from 2 to 6.

Moreover, with a vinylidene fluoride-trifluoroethylene copolymer and/or a vinylidene fluoride-tetrafluoroethylene copolymer, a melt flow rate at 230° C. is 0.03 g/min or less. More favorably, the melt flow rate is 0.02 g/min or less and, even more favorably, a highly-sensitive piezoelectric body thin film is obtained by using a polymeric piezoelectric body with a melt flow rate of 0.01 g/min or less.

Generally, when subjecting a film-like material to heat treatment, ends of the material are supported by chucks, clips, and the like and the material is placed in a predetermined temperature environment so that heat is applied onto a film surface in an efficient and uniform manner. In doing so, in case of a material that shrinks while being heated, applying heat in a configuration in which a heat source such as a heating plate comes into direct contact with the film surface adversely affects flatness and is therefore undesirable. Rather, performing a minor relaxation process with respect to thermal shrinkage during heating is more beneficial to flatness. The relaxation process involves varying stress at both ends of the film while tracking a contracting or expanding force which acts on the film during heat treatment and subsequent cooling down to room temperature. In the relaxation process, the film may be shrunk so as to alleviate stress or expanded in such a manner that the film does not stretch in a tensioned direction as long as the film does not relax to such a degree that flatness can no longer be maintained or the film does not break due to excessive stress. In the present embodiment, when a stretching direction is defined as a positive direction, stretching is performed by about 10% by length, and in the event that the film stretches during cooling, second-stage stretching is performed up to about 10% so as to follow slack. The second-stage stretching is performed by operating a stretching chuck to the extent that the slack of the film is eliminated and the film becomes tightly stretched. Further treatment causes stretching during cooling and may result in breaking the film.

In the heat treatment of the organic piezoelectric material according to the present embodiment, for the purpose of applying heat onto a film surface in an efficient and uniform manner, ends of the film are favorably supported by chucks, clips, and the like and the film is placed in a temperature environment not exceeding a temperature lower than a melting point of the film by 10° C. For example, in a case of a organic piezoelectric material containing polyvinylidene fluoride as a main component, since polyvinylidene fluoride has a melting point of 150 to 180° C., heat treatment is favorably performed in a temperature of 110 to 140° C. In addition, although effects of the heat treatment emerge after 30 minutes or more and the longer the duration, the greater the promotion of crystal growth, since saturation also proceeds with time, an actual duration of the heat treatment is around 10 hours and around a full day at the longest. Even during this period, the film is favorably subjected to a certain amount of stress in order to maintain the flatness of the film, From the perspective of final flatness, the tension during the heat treatment favorably ranges within 0.1 to 500 kPa and, more favorably, minimum stress is used as the tension. Since film during heat treatment is soft and stretches even farther when tension exceeds this value, the effect of the heat treatment may be lost and, at worst, the film may break.

A polarization treatment is performed by bonding electrodes to both surfaces of the organic piezoelectric material created as described above and, under compression by an insulating member, applying a voltage between the electrodes, Generally, a piezoelectric material is a material characteristically having a deformation response with respect to an electric field response, Therefore, a deformation response occurs even due to an electric field during a polarization treatment. In other words, deformation occurs due to an electric field even when a polarization treatment is being performed on a material by subjecting the material to the electric field in order to impart characteristics as a piezoelectric material. Therefore, materials sometimes deform after the polarization treatment and are unable to maintain their initial shapes. In consideration thereof, in the present embodiment, by performing a polarization treatment while applying compression in order to suppress such deformation during the polarization, an organic piezoelectric material is obtained which has less deformation and favorably retains its flatness before and after the polarization treatment and which has high piezoelectric characteristics.

In this case, a pressing force or, in other words, pressing pressure is favorably at least 0.98 (10 kg/cm$^2$) or higher and 9.8 MPa (100 kg/cm$^2$) or lower. This is because a force of 0.98 MPa (10 kg/cm$^2$) or higher enables suppression of deformation, and a force of 9.8 MPa (100 kg/cm$^2$) or lower prevents an occurrence of deformation in a thickness direction and enables an initial thickness to be retained or prevents short-circuiting of an impressed current during the polarization treatment. As a polarization treatment method according to the present embodiment, known voltage application methods such as direct voltage application and alternating voltage application may be applied.

The present embodiment will now be described using a specific example of an organic piezoelectric material. However, the present embodiment is not limited to the following example. In the present embodiment, P(VDF-TrFE) is used as the organic piezoelectric material. A composition method thereof is as follows, 70 parts (3000 g) of vinylidene fluoride (VDF; manufactured by Sigma-Aldrich Co, LLC), 30 parts of trifluoroethylene (TrFE; manufactured by Sigma-Aldrich Co. LLC.), 210 parts of pure water, 0.1 parts of methylcellulose (manufactured by Tokyo Chemical Industry Co., Ltd.), 0.2 parts of sodium pyrophosphate (manufactured by Taihei Chemical Industrial Ltd.), and 0.61 parts of dinormal propyl peroxyl dicarbonate (manufactured by NOF CORPORATION) were placed in a stainless-steel pressure-proof autoclave with an internal volume of 14 L, and polymerization was started at 25° C. 3.0 parts of ethyl acetate was added over a period of 3 hours and the polymerization reaction was continued. Subsequently, once internal pressure of the autoclave dropped to 25 kg/cm$^2$, unreacted material was recovered, and after sequentially repeating dehydration and aqueous washing of the polymeric substance three times, reduced-pressure drying was performed. The yield was 26%. An evaluation of the obtained P(VDF-TrFE) revealed a molecular weight of 255000 and a dispersion of 2.4.

Moreover, a weight-average molecular weight (Mn) and a molecular weight distribution (Mw/Mn) were calculated as described below by gel permeation chromatography (GPC), Measurement conditions were as follows.

Solvent: 30 mMLiBr in N-methylpyrrolidone
Instrument: HLC-8220GPC (manufactured by Tosoh Corporation)
Column: TSKgel SuperAWM-H×2 (manufactured by Tosoh Corporation)
Column temperature: 40° C.
Sample concentration: 1.0 g/L
Injection amount: 40 µl
Flow rate: 0.5 ml/min
Calibration curve: Standard polystyrene PS-1 (manufactured by Polymer Laboratories Ltd.); calibration curves of 9 samples within a range of Mw=580 to 2560000 were used.

Figure 26:
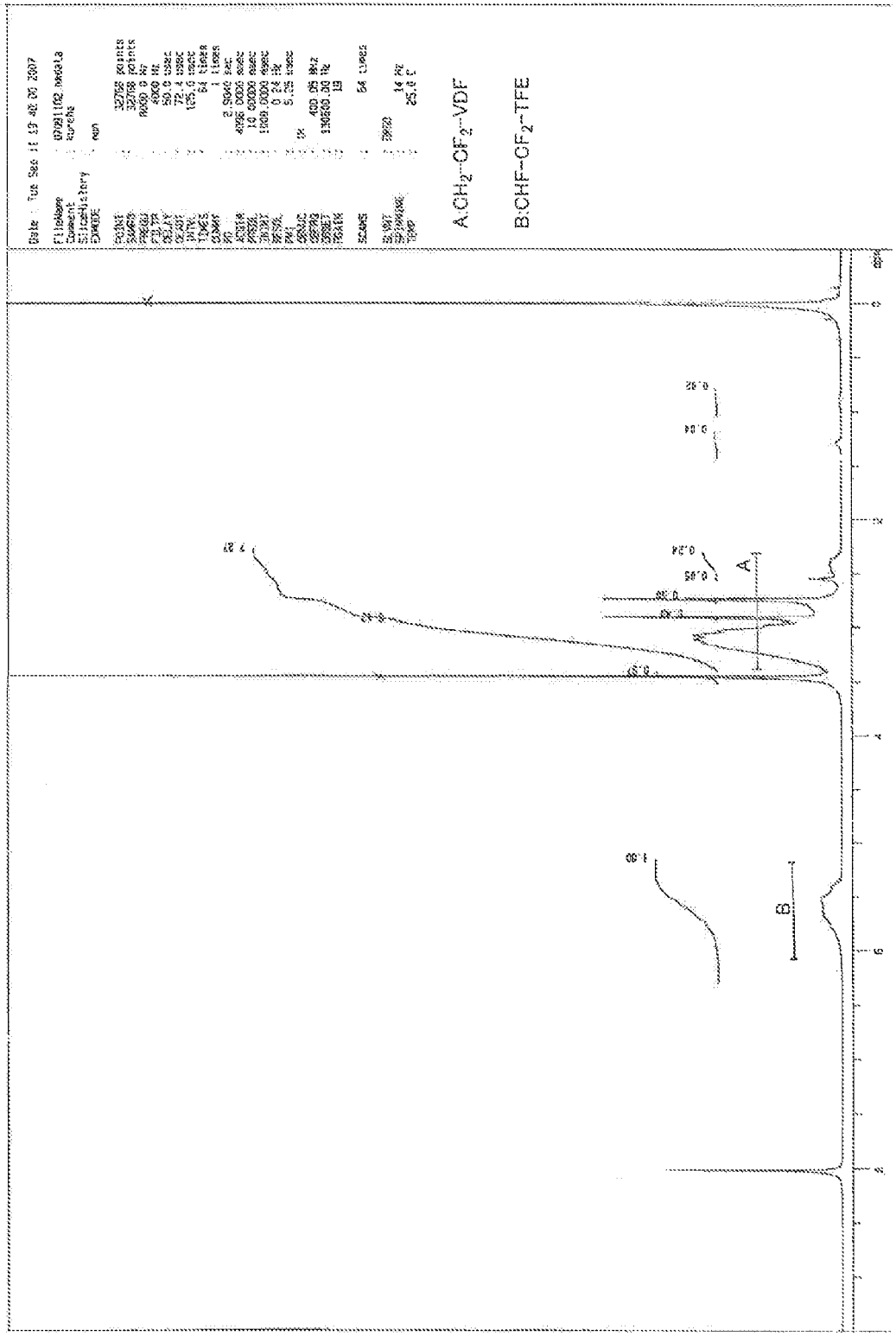
FIG. 26 is a graph showing an analysis result of organic piezoelectric, materials created to be used in the ultrasound transducer.

A composition was determined by 1H-NMR. A 3 wt % deuterated dimethylsulfoxide solution of the obtained P(VDF-TrFE) was prepared and placed in a sample tube, and analyzed at a frequency of 400 MHz by an NMR (nuclear magnetic resonance) device (Varian 400-MR, manufactured by Varian Medical Systems, Inc.). From an analysis of obtained data (refer to FIG. 26), VDF/TrFE=3/1 was determined based on a ratio of a signal of proton specific to TrFE that appears near 5.3 to 6.0 ppm and a signal of proton specific to VDF that appears near 2.3 to 3.3 ppm.

In a similar manner, PVDF that is a homopolymer of VDF was also polymerized. A GPC evaluation revealed a molecular weight of 200000 and a dispersion of 2.1.

The obtained P(VDF-TrFE) was applied on a glass plate using methyl ethyl ketone (manufactured by Kanto Chemical Co., Inc.) as a solvent to have a dried film thickness of 40±1 µm, and was dried for 30 minutes at 60° C. to fabricate an organic piezoelectric film.

In addition, after a chrome electrode with a thickness of 0.1 µm was formed by vapor deposition on a surface of the P(VDF-TrFE) (film thickness: 40±1 µm), a gold electrode with a thickness of 0.2 µm was formed by vapor deposition, the organic piezoelectric film was sandwiched by acrylic plates so that a pressure of 30 kgf/cm$^2$ was uniformly applied to the organic piezoelectric film with the exception of both ends thereof, and one of the electrode layers of the organic piezoelectric film was grounded while the other was connected to a function generator (20 MHz Function/Arbitrary Waveform Generator 33220A; manufactured by Agilent Technology) and a power amplifier (AC/DC AMPLIFIER HVA4321; manufactured by nF CORPORATION) so that a voltage is applied in a thickness direction of the organic piezoelectric film. Subsequently, under application of a 0.1 Hz sine wave, voltage was increased in 100 V increments every 20 seconds, and a maximum 100 MV/m electric field was applied to perform polling processing. Then, the electrodes were immersed in a 1% (methanol-pH4 sodium acetate aqueous solution) of 3-mercaptopropyl trimethoxy silane for 5 minutes, dried and than aqueously washed, dried once again, and then subjected to surface processing.

Three or six layers of this organic piezoelectric film were laminated so as to have a thickness including the electrodes of 0.12 mm and an overlapping portion (voltage application range) of the front and back electrodes of 3.3 mm. For the lamination, polarization directions of the organic piezoelectric films were set to a same direction, a same direction, and an opposite direction as shown in FIG. 16 described earlier in the case of three layers, and set to a same direction, a same direction, an opposite direction, an opposite direction, . . . as shown in FIG. 8 described, earlier in the case of six layers. Moreover, as comparative examples, a three-layer lamination with polarization directions set to a same direction, an opposite direction, and a same direction as shown in FIG. 18 described earlier, and a lamination using PZT that is an inorganic material were also created. An adhesive used during lamination was an epoxy-based resin, while applied pressure was 30 kgf/cm$^2$ and uniform in the thickness direction. After lamination, dicing was performed to cut out dices of 7.5 mm×50 mm, side electrodes were formed, and laminated piezoelectric bodies 1 to 4 and laminated piezoelectric bodies 5 and 6 were created.

An evaluation method of the laminated piezoelectric bodies 1 to 6 will now be described. First, the organic piezoelectric bodies themselves were evaluated. This was performed by sequentially adhering an electrode-patterned FPC onto side surfaces and adhering a backing layer with a thickness of 3.0 mm onto back surfaces of the laminated piezoelectric bodies 1 to 6, and then adhering an acoustic matching layer (ML layer) on an ultrasound wave emitting side (in cases of laminated piezoelectric bodies 1, 2, 5, and 6). Subsequently, dicing was performed at 0.15 mm intervals in a longitudinal direction using a blade with a thickness of 30 µm. Furthermore, an insulating layer of around 3 µm was provided by a parylene treatment, and in a case of laminating an acoustic matching layer, a lens was further adhered onto the insulating layer. Subsequently, a connector was connected to the FPC, and the ultrasound transducers created in this manner were placed in cases to create the ultrasound probes 1 to 6 capable of both transmission and reception.

Figure 27:
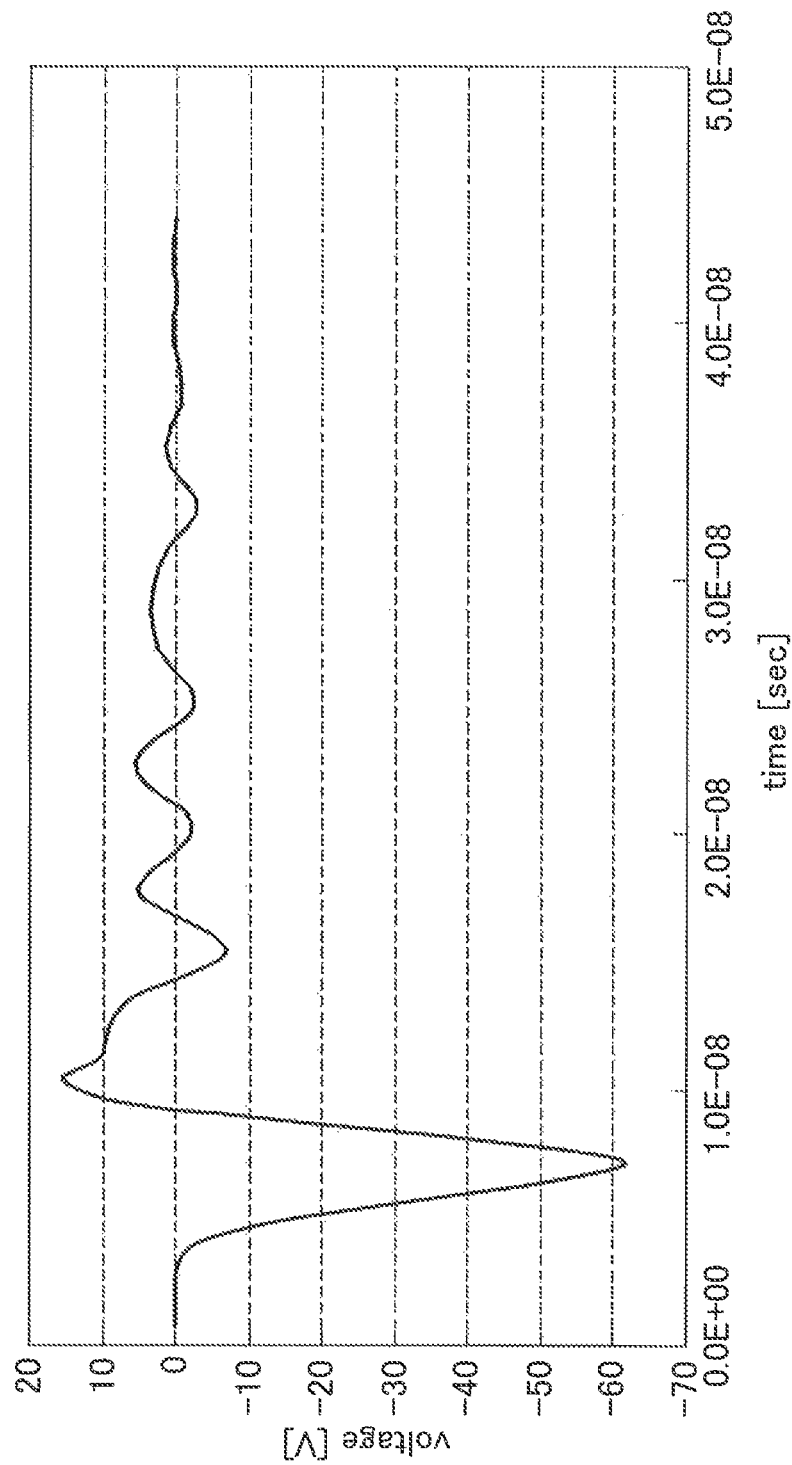
FIG. 27 is a graph showing a transmission waveform in a case of single pulse drive without coding.
Figure 28:
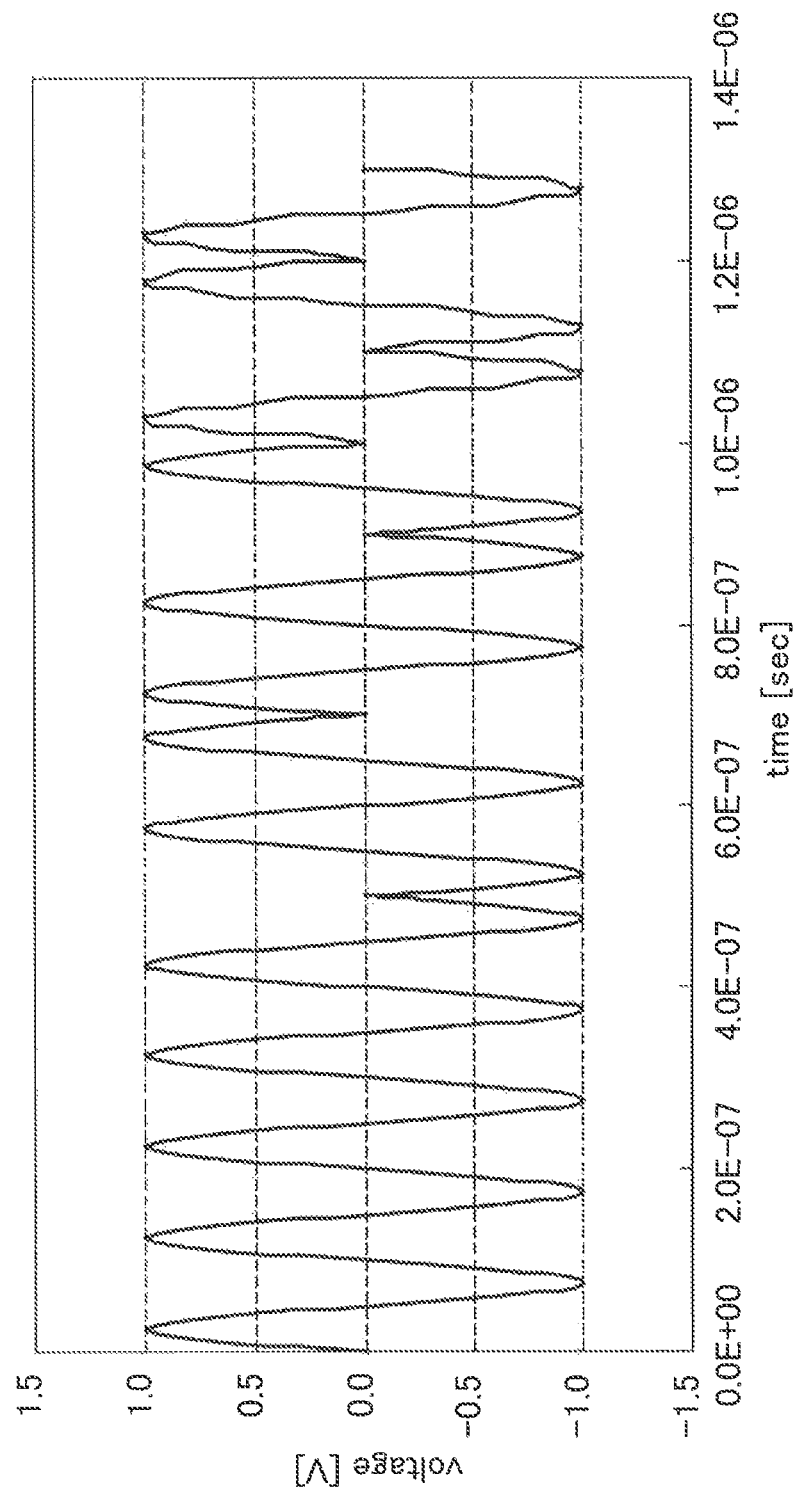
FIG. 28 is a graph showing a transmission signal waveform in a case of multiple pulse drive with coding.

A pulsar receiver (PANAMETRICS-NDT MODEL 5900PR, manufactured by Olympus Corporation, input impedance: 5000Ω) and an oscilloscope TPS5032, manufactured by Tektronix, Inc.) were connected to the ultrasound probes 1 to 6, the ultrasound probes 1 to 6 were placed in deaerated water, and a metallic reflector was arranged on an ultrasound wave emitting surface side. The ultrasound probes 1 to 6 were driven in two ways, namely, using a pulse without coding and using a coded pulse described in Japanese Patent Application Publication No. 2003-225237 described earlier. A received ultrasound wave was converted into an electrical signal and a voltage waveform thereof was observed by an oscilloscope. An alignment of the ultrasound probes and the reflector was determined as a coordinate where an effective value of the voltage waveform is maximum. Ultrasound waves were transmitted and received after the alignment. FIG. 27 shows a received waveform when coding was not performed, and FIG. 28 shows a received waveform when coding was performed. With respect to pulses obtained as described above, sensitivities with respect to fundamental waves were determined based on band characteristics acquired by FFT analysis performed on pulses subjected to pulse compression in cases where a coded pulse was used and on pulses without modification in cases where a coded pulse was not used. A result thereof is as shown in Table 1.

TABLE 1

| PROBE | TRANSMITTING/ RECEIVING MATERIAL | NUMBER OF LAMINATIONS | THICKNESS [µm] | POLARIZATION ARRANGEMENT | CODING | ML LAYER | TRANSMISSION FREQUENCY [MHz] | RECEPTION FREQUENCY [MHz] | TRANSMISSION/ RECEPTION SENSITIVITY [dB] |
|---|---|---|---|---|---|---|---|---|---|
| 1 | PVDF | 3 | 120 | FIG. 16 | NOT APPLIED | PRESENT | 15 | 15 | −33 |
| 2 | PZT | 3 | 240 | FIG. 16 | NOT APPLIED | PRESENT | 12 | 12 | −27 |
| 3 | PVDF | 3 | 120 | FIG. 16 | APPLIED | ABSENT | 15 | 15 | −21 |
| 4 | PVDF | 6 | 120 | FIG. 8 | APPLIED | ABSENT | 15 | 15 | −20 |
| 5 (COMPARATIVE EXAMPLE 1) | PVDF | 3 | 120 | FIG. 18 | NOT APPLIED | PRESENT | 18 | 18 | −39 |
| 6 (COMPARATIVE EXAMPLE 2) | PZT | 3 | 240 | FIG. 18 | NOT APPLIED | PRESENT | 10 | 10 | −35 |

The present results show that, by using the ultrasound probes 1 to 4 mounted with the laminated piezoelectric bodies 1 to 4 created by a lamination method having a regularity based on the concepts described earlier, a high-frequency wave that has been reflected in a living body can be received with high sensitivity and a diagnostic image with high definition and high resolution can be obtained.

Next, the laminated piezoelectric bodies 1 to 6 described above were mounted on an inorganic piezoelectric body, whereby an evaluation was performed as a mutually separate transmitter and receiver. In other words, an intermediate layer (IL) 24 exists in a structure shown in FIG. 24 in order to improve the passage of sound from an inorganic transmitting piezoelectric layer 23 to an upper receiving piezoelectric layer. Specifically, an electrode-patterned FPC was adhered onto side surfaces and a PZT layer with a central frequency of 5 MHz and a backing layer were adhered onto back surfaces of the laminated piezoelectric bodies 1 to 6 in sequence, and an acoustic matching layer was further adhered onto the ultrasound wave emitting side when necessary. Subsequently, dicing was performed at 0.15 mm intervals in a longitudinal direction using a blade with a thickness of 30 μm. Furthermore, an insulating layer of around 3 μm was provided by a parylene treatment, and in a case of laminating the acoustic matching layer, a lens was further adhered onto the insulating layer. Subsequently, a connector was connected to the FPC, and the ultrasound transducers created in this manner were placed in cases to create the ultrasound probes 1 to 6 in which a transmitter and a receiver are configured mutually separate.

The pulsar receiver and the oscilloscope described above were connected to the ultrasound probes 1 to 6 to perform experiments by the same method as described above. With respect to obtained pulses, sensitivities in a third order harmonic band were determined based on band characteristics acquired by FFT analysis performed on pulses subjected to pulse compression in cases where a coded pulse was used and on pulses without modification in cases where a coded pulse was not used. A result thereof is as shown in Table 2.

A laminated piezoelectric body according to one mode comprises: a plurality of mutually laminated piezoelectric bodies of equal thickness; a plurality of electrodes arranged at interlayers of the plurality of mutually laminated piezoelectric bodies and on surfaces of piezoelectric bodies at both ends; and two connecting wirings which mutually connect the respective piezoelectric bodies in parallel by coupling farther-side electrodes of mutually adjacent piezoelectric bodies, wherein each of the plurality of piezoelectric bodies arranges an orientation of residual polarization or a crystal axis that is related, to an electrical displacement or a sign of an electric field due to a direct piezoelectric effect in a direction which reduces sensitivity in a first resonance mode and increases sensitivity in a second resonance mode of a higher order than the first resonance mode with respect to an axis of a first-level piezoelectric body on a fixed end-side.

With the laminated piezoelectric body configured in this manner, since the respective piezoelectric bodies are arranged in a direction corresponding to a desired resonance mode, an output sound pressure during transmission or an output voltage during reception of a desired high-frequency component can be increased compared to those in a first order mode and electrical impedance can be reduced.

In addition, according to another mode, in the laminated piezoelectric body described above, favorably, the number of the plurality of piezoelectric bodies is two, and the respective piezoelectric bodies are arranged such that an orientation of residual polarization or a crystal axis that is related to an electrical displacement or a sign of an electric field due to a direct piezoelectric effect is in a same direction.

Furthermore, a laminated piezoelectric body manufacturing method according to another mode is a method of manufacturing a laminated piezoelectric body which includes piezoelectric bodies of equal thickness that are laminated in two layers and which transmits and receives an ultrasound wave of a third order harmonic component due to a 3λ/4

TABLE 2

| PROBE | RECEIVING MATERIAL | NUMBER OF LAMINATIONS | THICKNESS [μm] | POLARIZATION ARRANGEMENT | CODING | ML LAYER | TRANSMISSION FREQUENCY [MHz] | RECEPTION FREQUENCY [MHz] | RECEPTION SENSITIVITY OF THIRD ORDER HARMONIC [dB] |
|---|---|---|---|---|---|---|---|---|---|
| 1 | PVDF | 3 | 120 | FIG. 16 | NOT APPLIED | PRESENT | 5 | 15 | +15 |
| 2 | PZT | 3 | 240 | FIG. 16 | NOT APPLIED | PRESENT | 4 | 12 | +8 |
| 3 | PVDF | 3 | 120 | FIG. 16 | APPLIED | ABSENT | 5 | 15 | +30 |
| 4 | PVDF | 6 | 120 | FIG. 8 | APPLIED | ABSENT | 5 | 15 | +31 |
| 5 (COMPARATIVE EXAMPLE 1) | PVDF | 3 | 120 | FIG. 18 | NOT APPLIED | PRESENT | 6 | 18 | +6 |
| 6 (COMPARATIVE EXAMPLE 2) | PZT | 3 | 240 | FIG. 18 | NOT APPLIED | PRESENT | 3.3 | 10 | +2 |

The present results show that, by using the ultrasound probes 1 to 4 mounted with the laminated piezoelectric bodies 1 to 4 created by a lamination method having a regularity based on the concepts described earlier, third order harmonics generated in a living body can be received with high sensitivity and a diagnostic image with high definition and nigh resolution can be obtained.

While the present specification discloses techniques of various modes as presented above, primary techniques among such disclosed techniques are summarized as follows.

resonance created by an expansion and contraction of the thickness of the piezoelectric bodies, the method comprising: mutually connecting the respective piezoelectric bodies in parallel by coupling, among electrodes formed at an interlayer and on external surfaces of the respective piezoelectric bodies, electrodes on the external surfaces by a connecting wiring; and arranging both piezoelectric bodies such that an orientation of residual polarization or a crystal axis that is related to an electrical displacement or a sign of an electric field due to a direct piezoelectric effect is in a same direction.

With a two-layer laminated piezoelectric body and a manufacturing method thereof which are configured as described above, among electrodes formed at an interlayer and on external surfaces of the respective piezoelectric bodies, electrodes on the external surfaces are coupled by a connecting wiring in order to mutually connect the respective piezoelectric bodies in parallel. In addition, both piezoelectric bodies are arranged such that an orientation of residual polarization or a crystal axis that is related to an electrical displacement or a sign of an electric field due to a direct piezoelectric effect is in a same direction.

Therefore, with a two-layer laminated piezoelectric body configured as described above, an output sound pressure during transmission or an output voltage during reception of a third order harmonic component of a resonance in the $3\lambda/4$ resonance mode can be increased in comparison to a $\lambda/4$ resonance mode and a signal in a first order mode can be attenuated without using a filter, an amplifier, or the like. In addition, with a two-layer laminated piezoelectric body configured as described above, since the number of parallel piezoelectric bodies or, in other words, the number of laminations is two, electrical impedance can be reduced to $½$ which is advantageous to piezoelectric bodies with a low permittivity and a small capacitance such as an organic piezoelectric body. Furthermore, a manufacturing method configured as described above provides a two-layer laminated piezoelectric body that achieves such operational advantages.

Moreover, according to another mode, in the laminated piezoelectric body described above, favorably, the number of the plurality of piezoelectric bodies is three, and the respective piezoelectric bodies are arranged such that, with respect to an axis of a first-level piezoelectric body on a fixed end-side, an orientation of residual polarization or a crystal axis that is related to an electrical displacement or a sign of an electric field due to a direct piezoelectric effect is in a same direction for a second-level piezoelectric body that is in contact with the first-level piezoelectric body and in an opposite direction for a third-level piezoelectric body that is in contact with the second-level piezoelectric body.

In addition, a laminated piezoelectric body manufacturing method according to another mode is a method of manufacturing a laminated piezoelectric body which includes piezoelectric bodies of equal thickness that are laminated in a plurality of layers and which transmits and receives an ultrasound wave of a third order harmonic component due to a $3\lambda/4$ resonance created by an expansion and contraction of the thickness of the piezoelectric bodies, the method comprising: laminating the piezoelectric bodies in three layers; mutually connecting the respective piezoelectric bodies in parallel by coupling, among electrodes formed at interlayers of the respective piezoelectric bodies and on surfaces of the piezoelectric bodies at both ends, farther-side electrodes of mutually adjacent piezoelectric bodies by a connecting wiring; and arranging the respective piezoelectric bodies such that, with respect to an axis of a first-level piezoelectric body on a fixed end-side, an orientation of residual polarization or a crystal axis that is related to an electrical displacement or a sign of an electric field due to a direct piezoelectric effect is in a same direction for a second-level piezoelectric body that is in contact with the first-level piezoelectric body and in an opposite direction for a third-level piezoelectric body that is in contact with the second-level piezoelectric body.

With a three-layer laminated piezoelectric body and a manufacturing method thereof which are configured as described above, among electrodes formed at interlayers of the respective piezoelectric bodies and on surfaces of the piezoelectric bodies at both ends, further-side electrodes of mutually adjacent piezoelectric bodies are coupled by a connecting wiring in order to mutually connect the respective piezoelectric bodies in parallel in addition, the respective piezoelectric bodies are arranged such that, with respect to an axis of a first-level piezoelectric body on a fixed end-side, an orientation of residual polarization or a crystal axis that is related to an electrical displacement or a sign of an electric field due to a direct piezoelectric effect is in a same direction for a second-level piezoelectric body that is in contact with the first-level piezoelectric body and in an opposite direction for a third-level piezoelectric body that is in contact with the second-level piezoelectric body.

Therefore, with a three-layer laminated piezoelectric body configured as described above, an output sound pressure during transmission or an output voltage during reception of the third order harmonic component can be increased in comparison to a case of a $\lambda/4$ resonance mode and a signal in a first order mode can be attenuated without using a filter, an amplifier, or the like, in addition, with a three-layer laminated piezoelectric body configured as described above, since the number of parallel piezoelectric bodies or, in other words, the number of laminations is three, electrical impedance can be reduced to $⅓$ which is advantageous to piezoelectric bodies with a low permittivity and a small capacitance such as an organic piezoelectric body. Furthermore, a manufacturing method configured as described above provides a three-layer laminated piezoelectric body that achieves such operational advantages.

Moreover, according to another mode, in the laminated piezoelectric body described above, favorably, the number of the plurality of piezoelectric bodies is four or more, and the respective piezoelectric bodies are arranged to have a periodicity such that, with respect to an axis of a first-level piezoelectric body on a fixed end-side, an orientation of residual polarization or a crystal axis that is related to an electrical displacement or a sign of an electric field due to a direct piezoelectric effect for a second-level piezoelectric body that is in contact with the first-level piezoelectric body is in a same direction; and an orientation of residual polarization or a crystal axis that is related to an electrical displacement or a sign of an electric field due to a direct piezoelectric effect for a third-level piezoelectric body that is in contact with the second-level piezoelectric body, and for a fourth-level piezoelectric body is in an opposite direction. In addition, in the laminated piezoelectric body described above, favorably, an ultrasound wave in a resonance mode of a third or higher order is transmitted and received due to an expansion and contraction of the piezoelectric body in a thickness direction.

In addition, a laminated piezoelectric body manufacturing method according to another mode is a method of manufacturing a laminated piezoelectric body which includes piezoelectric bodies of equal thickness that are laminated in four or more layers, the method comprising; mutually connecting the plurality of piezoelectric bodies in parallel by coupling, among electrodes formed at interlayers of the respective laminated piezoelectric bodies and on surfaces of the piezoelectric bodies at both ends, farther-side electrodes of mutually adjacent piezoelectric bodies by a connecting wiring; and arranging the respective piezoelectric bodies to have a periodicity such that, with respect to an axis of a first-level piezoelectric body on a fixed end-side, an orientation of residual polarization or a crystal axis that is related to an electrical displacement or a sign of an electric field due to a direct piezoelectric effect for a second-level piezoelectric body that is in contact with the first-level piezoelectric body is in a same direction; and an orientation of residual polarization or a crystal axis that is related to an electrical displacement or a sign of an electric field due to a direct piezoelectric effect for a third-level piezoelectric body that is in contact with the second-level piezoelectric body, and for a fourth-level piezoelectric body is in an opposite direction.

With a laminated piezoelectric body having four or more layers and a manufacturing method thereof which are configured as described above, among electrodes formed at interlayers of the respective laminated piezoelectric bodies and on surfaces of the piezoelectric bodies at both ends, farther-side electrodes of mutually adjacent piezoelectric bodies are coupled by a connecting wiring in order to mutually connect the plurality of piezoelectric bodies in parallel. In addition, the respective piezoelectric bodies are arranged to have a periodicity such that, with respect to an axis of a first-level piezoelectric body on a fixed end-side, an orientation of residual polarization or a crystal axis that is related to an electrical displacement or a sign of an electric field due to a direct piezoelectric effect for a second-level piezoelectric body that is in contact with the first-level piezoelectric body is in a same direction; and an orientation of residual polarization or a crystal axis that is related to an electrical displacement or a sign of an electric field due to a direct piezoelectric effect for a third-level piezoelectric body that is in contact with the second-level piezoelectric body, and for a fourth-level piezoelectric body is in an opposite direction.

Therefore, with a laminated piezoelectric body having four or more layers configured as described above, an output sound pressure during transmission or an output voltage during reception of a harmonic component of a resonance in a high order resonance mode such as a 5λ/4 resonance mode can be increased in comparison to a λ/4 resonance mode and a signal in a first order mode can be attenuated without using a filter, an amplifier, or the like. In addition, with a laminated piezoelectric body having four or more layers configured as described above, if n denotes the number of parallel piezoelectric bodies or, in other words, the number of laminations, then electrical impedance can be reduced to 1/n which is advantageous to piezoelectric bodies with a low permittivity and a small capacitance such as an organic piezoelectric body. Furthermore, a manufacturing method configured as described above provides a laminated piezoelectric body having four or more layers which achieves such operational advantages.

Moreover, according to another mode, in the laminated piezoelectric bodies described above, favorably, each of the piezoelectric bodies is further split into two piezoelectric bodies in a thickness direction and the two piezoelectric bodies are mutually connected in parallel to constitute one set to be laminated, and for each of the split piezoelectric bodies, front and back sides of the piezoelectric body are reversed so that the orientation of the residual polarization or the crystal axis is consistent with an electrical displacement or a sign of an electric field in a distortion distribution within the laminated piezoelectric bodies.

In addition, according to another mode, in the laminated piezoelectric body manufacturing methods described above, favorably, each of the piezoelectric bodies is further split into two piezoelectric bodies in a thickness direction and the two piezoelectric bodies are mutually connected in parallel to constitute one set to be laminated, and for each of the split piezoelectric bodies, front and back sides of the piezoelectric body are reversed so that the orientation of the residual polarization or the crystal axis is consistent with an electrical displacement or a sign of an electric field in a distortion distribution within the laminated piezoelectric bodies.

With a laminated piezoelectric body and a manufacturing method thereof configured as described above, each of the piezoelectric bodies is split into two piezoelectric bodies which are mutually connected in parallel to be handled as one set.

Therefore, a laminated piezoelectric, body configured as described above is capable of further reducing electrical impedance by half and, at the same time, since electrodes at both ends assume a same potential, the entire laminated piezoelectric body can be electrically shielded. In addition, a manufacturing method configured as described above provides a laminated piezoelectric body that achieves such operational advantages.

Furthermore, an ultrasound transducer according to another mode uses any of the laminated piezoelectric bodies described above.

An ultrasound transducer with such a configuration is capable of increasing an output sound pressure during transmission or an output voltage during reception of a harmonic component in comparison to a case of a λ4 resonance mode, attenuating a signal in a first order mode, and reducing electrical impedance without using a filter, an amplifier, or the like.

Moreover, an ultrasound diagnostic device according to another mode comprises: an ultrasound transducer which transmits an Ultrasound wave into a subject that is a measurement object and which receives an ultrasound wave originating from the subject; a transmitting unit which supplies a transmission ultrasound signal to the ultrasound transducer; a receiving unit which performs predetermined signal processing on a reception signal received by the ultrasound transducer; and an image processing unit which creates a tomographic image of an internal state of the subject based on the reception signal from the receiving unit, wherein the ultrasound transducer is a laminated piezoelectric body including: a plurality of mutually laminated piezoelectric bodies of equal thickness; a plurality of electrodes arranged at interlayers of the plurality of mutually laminated piezoelectric bodies and on surfaces of piezoelectric bodies at both ends; and two connecting wirings which mutually connect the respective piezoelectric bodies in parallel by coupling farther-side electrodes of mutually adjacent piezoelectric bodies, wherein each of the plurality of piezoelectric bodies arranges an orientation of residual polarization or a crystal axis that is related to an electrical displacement or a sign of an electric field due to a direct piezoelectric effect in a direction which reduces sensitivity in a first resonance mode and increases sensitivity in a second resonance mode of a higher order than the first resonance mode with respect to an axis of a first-level piezoelectric body on a fixed end-side.

With an ultrasound diagnostic device configured in this manner, since the ultrasound transducer arranges the respective piezoelectric bodies in a direction corresponding to a desired resonance mode, an output sound pressure during transmission or an output voltage during reception of a desired high-frequency component can be increased compared to those in a first order mode and electrical impedance can be reduced. Therefore, an ultrasound diagnostic device configured as described above enables easier impedance matching and improves S/N.

In addition, according to another mode, in the ultrasound diagnostic device described above, favorably, the number of the plurality of piezoelectric bodies in the ultrasound transducer is two, and the respective piezoelectric bodies in the ultrasound transducer are arranged such that an orientation of residual polarization or a crystal axis that is related to an electrical displacement or a sign of an electric field due to a direct piezoelectric effect is in a same direction.

With an ultrasound diagnostic device configured as described above, an ultrasound transducer is configured so as to comprise a two-layer laminated piezoelectric body and, in order to transmit and receive an ultrasound wave of a third order mode component, an orientation of residual polarization or an orientation of a C axis or an A axis of crystals of each piezoelectric body is conformed to an electrical displacement or a sign of an electric field due to a direct piezoelectric effect. Therefore, an ultrasound diagnostic device configured as described above comprises a two-layer laminated piezoelectric body and is capable of effectively transmitting and receiving ultrasound waves of a third order mode component and reducing electrical impedance.

Moreover, according to another mode, in the ultrasound diagnostic device described above, favorably, the number of the plurality of piezoelectric bodies in the ultrasound transducer is three, and the respective piezoelectric bodies in the ultrasound transducer are arranged such that, with respect to an axis of a first-level piezoelectric body on a fixed end-side, an orientation of residual polarization or a crystal axis that is related to an electrical displacement or a sign of an electric field due to a direct piezoelectric effect is in a same direction for a second-level piezoelectric body that is in contact with the first-level piezoelectric body and in an opposite direction for a third-level piezoelectric body that is in contact with the second-level piezoelectric body.

With an ultrasound diagnostic device configured as described above, an ultrasound transducer is configured so as to comprise a three-layer laminated piezoelectric, body and, in order to transmit and receive an ultrasound wave of a third order mode component, an orientation of residual polarization or an orientation of a C axis or an A axis of crystals of each piezoelectric body is conformed to an electrical displacement or a sign of an electric field due to a direct piezoelectric effect. Therefore, an ultrasound diagnostic device configured as described above comprises a three-layer laminated piezoelectric body and is capable of effectively transmitting and receiving ultrasound waves of a third order mode component and reducing electrical impedance.

Furthermore, according to another mode, in the ultrasound diagnostic device described above, favorably, the number of the plurality of piezoelectric bodies in the ultrasound transducer is four or more, and the respective piezoelectric bodies in the ultrasound transducer are arranged to have a periodicity such that, with respect to an axis of a first-level piezoelectric body on a fixed end-side, an orientation of residual polarization or a crystal axis that is related to an electrical displacement or a sign of an electric field due to a direct piezoelectric effect for a second-level piezoelectric body that is in contact with the first-level piezoelectric body is in a same direction; and an orientation of residual polarization or a crystal axis that is related to an electrical displacement or a sign of an electric field due to a direct piezoelectric effect for a third-level piezoelectric body that is in contact with the second-level piezoelectric body, and for a fourth-level piezoelectric body is in an opposite direction.

With an ultrasound diagnostic device configured as described above, an ultrasound transducer is configured so as to comprise a laminated piezoelectric body having four or more layers and, in order to transmit and receive an ultrasound wave of a third order mode component, an orientation of residual polarization or an orientation of a C axis or an A axis of crystals of each piezoelectric body is conformed to an electrical displacement or a sign of an electric field due to a direct piezoelectric effect. Therefore, an ultrasound diagnostic device configured as described above comprises a laminated piezoelectric body having four or more layers and is capable of effectively transmitting and receiving ultrasound waves of a third order mode component and reducing electrical impedance.

Moreover, according to another mode, in the ultrasound diagnostic devices described above, favorably, the laminated piezoelectric body in the ultrasound transducer is used for both transmitting and receiving ultrasound waves, and the ultrasound transducer transmits an ultrasound wave in a $3\lambda/4$ resonance mode.

According to the configuration described above, an ultrasound diagnostic device is realized comprising an ultrasound probe which uses a $3\lambda/4$ resonance mode for both transmission and reception and which is suitable for high-frequency waves or, in other words, high resolution imaging.

In addition, according to another mode, in the ultrasound diagnostic devices described above, favorably, the laminated piezoelectric body in the ultrasound transducer is used for receiving an Ultrasound wave as a first piezoelectric body, the ultrasound transducer further includes a second piezoelectric body that transmits an ultrasound wave of a fundamental wave component in a $\lambda/4$ resonance mode, and the second piezoelectric body and the first piezoelectric body are laminated in this order from a side of a rear layer.

According to the configuration described above, an ultrasound diagnostic device is realized comprising an ultrasound probe which is capable of respectively using suitable piezoelectric bodies for transmission and reception and which is suitable for harmonic imaging in which large power transmission is performed and harmonics generated by a subject are received at high gain.

Furthermore, according to another mode, in the ultrasound diagnostic devices described above, favorably, the laminated piezoelectric body in the ultrasound transducer is used for receiving an ultrasound wave as a first piezoelectric body, the ultrasound transducer further includes two second piezoelectric bodies that transmit an ultrasound wave of a fundamental wave component in a $\lambda/4$ resonance mode, and the second piezoelectric bodies are provided in parallel on both sides of the first piezoelectric body.

According to the configuration described above, an ultrasound diagnostic device is realized comprising an ultrasound probe which is capable of respectively using suitable piezoelectric bodies for transmission and reception and which is suitable for harmonic imaging in which large power transmission is performed and harmonics generated by a subject are received at high gain.

Moreover, according to another mode, in the ultrasound diagnostic devices described above, favorably, the first piezoelectric body is made of a material containing an organic polymer as a main component.

According to the configuration described above, an organic polymer piezoelectric body is capable of handing a high-frequency signal and is suitable for receiving the harmonics, Therefore, an ultrasound diagnostic device is realized comprising an ultrasound probe which is suitable for harmonic imaging in which large power transmission is performed and harmonies generated by a subject are received at high gain as described above by using an organic piezoelectric body for reception.

In addition, according to another mode, in the ultrasound diagnostic devices described above, favorably, the second piezoelectric body is made of an inorganic material, the first piezoelectric body is made of a material containing an organic polymer as a main component, and a member for acoustic matching purposes is not interposed between the first piezoelectric body and a subject.

According to the configuration described above, among the laminated inorganic and organic piezoelectric bodies, since a subject side piezoelectric body is an organic piezoelectric body with low acoustic impedance, a member for acoustic impedance matching purposes can be omitted from between a subject such as a living body and the organic piezoelectric body. Therefore, with an ultrasound diagnostic device configured as described above, since an acoustic matching layer for impedance matching can be eliminated from between the organic piezoelectric body and the subject in the ultrasound transducer, a structure of the ultrasound transducer can be simplified.

Furthermore, according to another mode, in the ultrasound diagnostic devices described above, favorably, the transmitting unit supplies a transmission signal to the laminated piezoelectric body in the ultrasound transducer as a coded pulse voltage, and the receiving unit performs pulse compression on a signal received by the laminated piezoelectric body in the ultrasound transducer and causes the image processing unit to perform imaging on the pulse compressed signal.

With an ultrasound diagnostic device configured as described above, an ultrasound transducer thereof is capable of obtaining a reception pulse with a large amplitude or, in other words, favorable S/N while preventing an impact on a subject from becoming significant.

The present application is based on and claims priority to Japanese Patent Application No. 2010-84018, filed on Mar. 31, 2010, and Japanese Patent Application No. 2010-84533, filed on Mar. 31, 2010, the contents of which are incorporated by reference herein.

While the present invention has been described above as related to preferred embodiments in an appropriate and sufficient manner with reference to the accompanying drawings, it is to be understood that modifications and/or variations will be apparent to those skilled in the art. Therefore, it is to be understood that unless modifications or variations that are made by those skilled in the art depart from the scope of rights of the invention as set forth in the claims, all such modifications or variations are encompassed in the scope of rights of the invention.

INDUSTRIAL APPLICABILITY

According to the present invention, it is possible to provide a laminated piezoelectric body, a laminated piezoelectric body manufacturing method, and an ultrasound transducer and an Ultrasound diagnostic device that use the laminated piezoelectric body.

The invention claimed is:

1. An ultrasound transducer comprising:
only three mutually laminated piezoelectric layers of equal thickness;
a plurality of electrodes arranged at interlayers of the mutually laminated piezoelectric layers and on surfaces of piezoelectric layers at both ends; and
two connecting wirings which mutually connect the respective piezoelectric layers in parallel by coupling farther-side electrodes of mutually adjacent piezoelectric layers, wherein
a first-level piezoelectric layer of the laminated piezoelectric layers includes a fixed end-side and an opposite side on which the others of the piezoelectric layers are laminated,
the respective piezoelectric layers are arranged such that an orientation of the residual polarization or the crystal axis of the first-level piezoelectric layer is in a first direction, an orientation of the residual polarization or the crystal axis is in the first direction for a second-level piezoelectric layer that is in contact with the first-level piezoelectric layer and in a second direction, which is an opposite direction to the first direction, for a third-level piezoelectric layer that in contact with the second-level piezoelectric layer, and
the mutually laminated piezoelectric layers transmit an ultrasound wave into a subject and receive an ultrasound wave from the subject.

2. The ultrasound transducer according to claim 1, wherein each of the piezoelectric layers is further split into two piezoelectric layers in a thickness direction and the two piezoelectric layers are mutually connected in parallel to constitute one set to be laminated, and
for each of the split piezoelectric layers, front and back sides of the piezoelectric layer are reversed so that the orientation of the residual polarization or the crystal axis is consistent with an electrical displacement or a sign of an electric field in a distortion distribution within the laminated piezoelectric layers.

3. The ultrasound transducer according to claim 1, wherein the fixed-end side of file first-level piezoelectric layer is fixed to a rear layer by sandwiching the electrode therebetween, and defines a fixed end in a vibration of the first-level piezoelectric layer.

4. An ultrasound transducer comprising:
only six mutually laminated piezoelectric layers of equal thickness;
a plurality of electrodes arranged at interlayers of the mutually laminated piezoelectric layers and on surfaces of piezoelectric layers at both ends; and
two connecting wirings which mutually connect the respective piezoelectric layers in parallel by coupling farther-side electrodes of mutually adjacent piezoelectric layers, wherein
a first-level piezoelectric layer of the laminated piezoelectric layers includes a fixed end-side and an opposite side on which the others of the piezoelectric layers are laminated,
the respective piezoelectric layers are arranged to have a periodicity such that an orientation of the residual polarization or the crystal axis of the first-level piezoelectric layer is in a first direction, an orientation of a residual polarization or a crystal axis for a second-level piezoelectric layer that is in contact with the first-level piezoelectric layer is in the first direction; and an orientation of a residual polarization or a crystal axis for a third-level piezoelectric layer that is in contact with the second-level piezoelectric layer, and for a fourth-level piezoelectric layer that is in contact with the third-level piezoelectric layer is in a second direction, which is an opposite direction to the first direction, and an orientation of a residual polarization or a crystal axis for a fifth-level piezoelectric layer that is in contact with the fourth-level piezoelectric layer, and for a sixth-level piezoelectric layer that is in contact with the fifth-level piezoelectric layer is in the first direction, and
the mutually laminated piezoelectric layers transmit an ultrasound wave into a subject and receive an ultrasound wave from the subject.

5. The ultrasound transducer according to claim 4, wherein each of the plurality of piezoelectric layers is arranged such that each orientation of a residual polarization or a crystal axis in the each of the plurality of piezoelectric layers is in a direction which reduces sensitivity in a first resonance mode and increases sensitivity in a second resonance mode of a higher order than the first resonance mode with respect to the orientation of the residual polarization or the crystal axis of the first-level piezoelectric layer, and wherein the second resonance mode is a resonance mode of a third or higher order created by an expansion and contraction of the laminated piezoelectric layers in a thickness direction.

6. An ultrasound diagnostic device comprising:

an ultrasound transducer which transmits an ultrasound wave into a subject that is a measurement object and which receives an ultrasound wave originating from the subject;

a transmitting unit which supplies a transmission ultrasound signal to the ultrasound transducer;

a receiving unit which performs predetermined signal processing on a reception signal received by the ultrasound transducer; and an image processing unit which creates a tomographic image of an internal state of the subject based on the reception signal from the receiving unit, wherein the ultrasound transducer is a laminated piezoelectric body including:

only three mutually laminated piezoelectric layers of equal thickness; a plurality of electrodes arranged at interlayers of the mutually laminated piezoelectric layers and on surfaces of piezoelectric layers at both ends; and two connecting wirings which mutually connect the respective piezoelectric layers in parallel by coupling farther-side electrodes of mutually adjacent piezoelectric layers, wherein a first-level piezoelectric layer of the laminated piezoelectric layers includes a fixed end-side and an opposite side on which the others of the piezoelectric layers are laminated, the respective piezoelectric layers in the ultrasound transducer are arranged such that an orientation of the residual polarization or a crystal axis of the first-level piezoelectric layer on a fixed end-side is in a first direction, an orientation of a residual polarization or a crystal axis is in the first direction for a second-level piezoelectric layer that is in contact with the first-level piezoelectric layer and in a second direction, which is an opposite direction to the first direction, for a third-level piezoelectric layer that is in contact with the second-level piezoelectric layer, and the mutually laminated piezoelectric layers being configured to at least one of transmit an ultrasound wave into a subject and receive an ultrasound wave from the subject.

7. The ultrasound diagnostic device according to claim 6, wherein the laminated piezoelectric body in the ultrasound transducer is used for both transmitting and receiving ultrasound waves, and the ultrasound transducer transmits an ultrasound wave in a $3\lambda/4$ resonance mode.

8. The ultrasound diagnostic device according to claim 6, wherein the laminated piezoelectric body in the ultrasound transducer is used for receiving an ultrasound wave as a first piezoelectric body, the ultrasound transducer further includes a second piezoelectric body that transmits an ultrasound wave of a fundamental wave component in a $\lambda/4$ resonance mode, and the second piezoelectric body and the first piezoelectric body are laminated in this order from a side of a rear layer.

9. The ultrasound diagnostic device according to claim 8, wherein the first piezoelectric body is made of a material containing an organic polymer as a main component.

10. The ultrasound diagnostic device according to claim 8, wherein the second piezoelectric body is made of an inorganic material, the first piezoelectric body is made of a material containing an organic polymer as a main component, and a member for acoustic matching purposes is not interposed between the first piezoelectric body and the subject.

11. The ultrasound diagnostic device according to claim 6, wherein the laminated piezoelectric body in the ultrasound transducer is used for receiving an ultrasound wave as a first piezoelectric body, the ultrasound transducer further includes two second piezoelectric bodies that transmit an ultrasound wave of a fundamental wave component in a $\lambda/4$ resonance mode, and the second piezoelectric bodies are provided in parallel on both sides of the first piezoelectric body.

12. The ultrasound diagnostic device according to claim 6, wherein the transmitting unit supplies a transmission signal to the laminated piezoelectric body in the ultrasound transducer as a coded pulse voltage, and the receiving unit performs pulse compression on the reception signal received by the laminated piezoelectric body in the ultrasound transducer and causes the image processing unit to process the pulse-compressed signal.

13. The ultrasound diagnostic device according to claim 6, wherein the fixed-end side of the first-level piezoelectric layer is fixed to a rear layer by sandwiching the electrode therebetween, and defines a fixed end in a vibration of the first-level piezoelectric layer.

14. A ultrasound diagnostic device comprising:

an ultrasound transducer which transmits an ultrasound wave into a subject that is a measurement object and which receives an ultrasound wave originating from the subject;

a transmitting unit which supplies a transmission ultrasound signal to the ultrasound transducer;

a receiving unit which performs predetermined signal processing on a reception signal received by the ultrasound transducer; and an image processing unit which creates a tomographic image of an internal state of the subject based on the reception signal from the receiving unit, wherein the ultrasound transducer is a laminated piezoelectric body including:

only six mutually laminated piezoelectric layers of equal thickness; a plurality of electrodes arranged at interlayers of the mutually laminated piezoelectric layers and on surfaces of piezoelectric layers at both ends; and two connecting wirings which manually connect the respective piezoelectric layers in parallel by coupling farther-side electrodes of mutually adjacent piezoelectric layers, wherein a first-level piezoelectric layer of the laminated piezoelectric layers includes a fixed end-side and an opposite side on which the others of the piezoelectric layers are laminated, the respective piezoelectric layers in the ultrasound transducer are arranged such that an orientation of the residual polarization or the crystal axis of the first-level piezoelectric layer on a fixed end-side is in a first direction, an orientation of a residual polarization or a crystal axis for a second-level piezoelectric layer that is in contact with the first-level piezoelectric layer is in the first direction; and an orientation of a residual polarization or a crystal axis for a third-level piezoelectric layer that is in contact with the second-level piezoelectric layer, and for a fourth-level piezoelectric layer that is in contact with the third-level piezoelectric layer is in a second direction, which is an opposite direction to the first direction, and an orientation of a residual polarization or a crystal axis for a fifth-level piezoelectric layer that is in contact with the fourth-level piezoelectric layer, and for sixth-level piezoelectric layer that is in contact with the fifth-level piezoelectric layer is in the first direction, and the mutually laminated piezoelectric layers transmit an ultrasound wave into a subject and receive an ultrasound wave from the subject.

* * * * *